(12) United States Patent
Amelio et al.

(10) Patent No.: US 11,152,794 B2
(45) Date of Patent: *Oct. 19, 2021

(54) MULTIPURPOSE ELECTRICAL FIXTURES

(71) Applicant: 286 Two LLC, Spring Valley, NY (US)

(72) Inventors: Paul Amelio, New York, NY (US);
Alfonso Amelio, New York, NY (US);
David Katz, New York, NY (US)

(73) Assignee: 286 Two LLC, Monsey, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,853

(22) Filed: Nov. 11, 2019

(65) Prior Publication Data
US 2020/0083718 A1    Mar. 12, 2020

Related U.S. Application Data

(63) Continuation of application No. 15/633,712, filed on Jun. 26, 2017, now Pat. No. 10,476,276.
(Continued)

(51) Int. Cl.
*H02J 5/00* (2016.01)
*A61L 9/20* (2006.01)
(Continued)

(52) U.S. Cl.
CPC ................... *H02J 5/00* (2013.01);
*A61L 9/18* (2013.01); *A61L 9/20* (2013.01);
*B66F 3/38* (2013.01); *G08C 17/02* (2013.01);
*H02J 50/20* (2016.02); *H02J 50/40* (2016.02);
*A61L 2209/12* (2013.01); *H02J 50/50* (2016.02)

(58) Field of Classification Search
CPC .... H02J 5/00; H02J 50/20; H02J 50/40; H02J 50/50; A61L 9/18; A61L 9/20; A61L 2209/12; B66F 3/38; G08C 17/02
See application file for complete search history.

(56) References Cited

U.S. PATENT DOCUMENTS 2,609,170 A    9/1952 Farrington et al.
4,316,238 A    2/1982 Booty et al.
(Continued)

OTHER PUBLICATIONS

Invitation to Pay Additional Fees issued by the International Searching Authority dated Aug. 31, 2017, issued in connection with International Application No. PCT/US2017/039332.
(Continued)

*Primary Examiner* — Robert L Deberadinis
(74) *Attorney, Agent, or Firm* — Pearl Cohen Zedek Latzer Baratz LLP

(57) ABSTRACT

A multipurpose electrical assembly is provided that includes a module receiving an alternating current from a power source in a ceiling and converting the alternating current source to a direct current source. The multipurpose electrical assembly also includes a plurality of devices each having a first connector on a first surface for connecting to the assembly and receiving electrical power from a preceding device and a second connector on a second opposing surface for receiving a following device to be connected to the assembly and for transferring electrical power to the following device. A first device of the plurality of devices attaches to the module, and the plurality of devices can be arranged in any order.

47 Claims, 26 Drawing Sheets

Related U.S. Application Data

(60) Provisional application No. 62/354,614, filed on Jun. 24, 2016, provisional application No. 62/373,148, filed on Aug. 10, 2016.

(51) Int. Cl.
  *H02J 50/20* (2016.01)
  *H02J 50/40* (2016.01)
  *A61L 9/18* (2006.01)
  *B66F 3/38* (2006.01)
  *G08C 17/02* (2006.01)
  *H02J 50/50* (2016.01)

(56) References Cited

U.S. PATENT DOCUMENTS

| | | |
|---|---|---|
| 4,694,285 A | 9/1987 | Scripps |
| 5,980,057 A | 11/1999 | Christie |
| 6,142,439 A | 11/2000 | Aramaki |
| 10,476,276 B2 * | 11/2019 | Amelio ................ H02J 50/20 |
| 2004/0218394 A1 | 11/2004 | Kim |
| 2007/0177375 A1 | 8/2007 | Petzl et al. |
| 2009/0278480 A1 | 11/2009 | Nunes |
| 2012/0021623 A1 | 1/2012 | Gorman |
| 2014/0158917 A1 | 6/2014 | Stibich et al. |
| 2015/0198311 A1 | 7/2015 | O'Brien et al. |
| 2015/0288448 A1 | 10/2015 | Masarik |
| 2016/0091179 A1 | 3/2016 | Jiang et al. |

OTHER PUBLICATIONS

International Search Report of the International Searching Authority dated Nov. 13, 2017, issued in connection with International Application No. PCT/US2017/039332.

Written Opinion of the International Searching Authority dated Nov. 13, 2017, issued in connection with International Application No. PCT/US2017/039332.

* cited by examiner

MULTIPURPOSE ELECTRICAL FIXTURES

RELATED APPLICATIONS

This application claims priority to U.S. Provisional Patent Application Ser. No. 62/354,614 filed on Jun. 24, 2016 and U.S. Provisional Patent Application Ser. No. 62/373,148 filed on Aug. 10, 2016, and is a continuation of, and claimed priority to, U.S. patent application Ser. No. 15/633,712 filed on Jun. 26, 2017, now U.S. Pat. No. 10,476,276, the entire disclosures of which are hereby expressly incorporated by reference.

FIELD OF THE DISCLOSURE

The present disclosure relates to electrical fixtures for various uses. More particularly, the present disclosure relates to multipurpose electrical fixtures.

RELATED ART

A structure hanging from a ceiling is normally installed with one purpose, such as a ceiling fan. If a ceiling fan is no longer desired, there is a significant cost and hassle in replacing the ceiling fan with a new structure for a different purpose.

Moreover, a ceiling fixture typically can serve one purpose, or a limited number of purposes. For example, a ceiling fan can only blow air in a room. There can be a significant cost and space saving in a room if many devices are mounted on ceiling structure. For example, a hospital room has many devices which may take up a lot of space. For example, hospitals currently use disinfection devices such as a UV light for sterilizing a room. Hospitals also need a speaker or microphone to communicate with patients. Hospitals may further require drones for deliver medicines to patients or cameras for monitoring patient activity. Hospitals may further require air sanitization devices for filtering air.

Still further, hospital solutions for sanitizing using UV-light can be harmful to staff and patients. The location of such devices on the side of a room can limit its effectiveness.

Therefore, there exists need for a multipurpose electrical fixtures that can house a number of devices for serving various purposes.

SUMMARY

In a first embodiment, a multipurpose electrical assembly is provided that includes an antenna extending vertically downward from a ceiling for receiving a plurality of devices and a hydraulic lift being operable to move the antenna in a vertical direction. The antenna receives electrical power from a power source in the ceiling and distributes power to the plurality of devices and the plurality of devices can be arranged in any order.

In a second embodiment, a multipurpose electrical assembly includes a plurality of devices each having a connector on a first surface for connecting to the assembly and a plurality of pins on a second opposing surface for receiving a device to be connected to the assembly. The device also includes a member mechanically fastened to a ceiling having a plurality of pins for receiving a first device of the plurality of devices. The connector of the plurality of devices receives electrical power from a preceding device and transfers electrical power to a following device through the plurality of pins and the plurality of devices can be arranged in any order.

In a third embodiment, a lighting system is provided which includes a plurality of recesses in a ceiling having a first connector, a plurality of drones each having an LED light and a second connector for connecting to the first connector and docking in the recess, and a remote computer system for automatically controlling the plurality of drones to dock in the recess where light is required.

In a fourth embodiment, a multipurpose electrical assembly is provided which includes a cable extending vertically downward from a ceiling, a power lift being operable to move the cable in a vertical direction, a plurality of devices mechanically fastened with a plurality of superstack devices, and wherein the plurality of devices can be arranged in any order.

In a fifth embodiment, a multipurpose electrical assembly is provided that includes a module receiving an alternating current from a power source in a ceiling and converting the alternating current source to a direct current source, a plurality of devices each having a first connector on a first surface for connecting to the assembly and receiving electrical power from a preceding device and a second connector on a second opposing surface for receiving a following device to be connected to the assembly and for transferring electrical power to the following device, a first device of the plurality of devices attaches to the module, and wherein the plurality of devices can be arranged in any order.

Still other embodiments of the multipurpose electrical assembly are disclosed hereinbelow in greater detail.

BRIEF DESCRIPTION OF THE DRAWINGS

The foregoing features of the disclosure will be apparent from the following Detailed Description, taken in connection with the accompanying drawings, in which.

DETAILED DESCRIPTION

The present disclosure relates to multipurpose electrical fixtures, as discussed in detail below in connection with FIGS. 1-26.

The present disclosure describes particular uses for a multipurpose electrical fixtures. However, the present disclosure is not limited to any use for the electrical fixture assembly. Indeed, the electrical fixtures uses include, but is not limited to, load control, coordinator functions, security, safety, enhanced vision to capture the full circumference of a room, motion detection, biometrics, thermal detection, daylight harvesting, $CO_2$/carbon reduction, energy efficiency, renewable energy uses, water utilization efficiency, natural resource conservation, identification of wastage, health and wellness, ambient monitoring and control, air quality, lighting, reduction of cancer, detoxification/air-purification, vertical farming, low impact food-supply chain, control of vertical greenhouse gases, and skilled work force uses.

Figure 1:
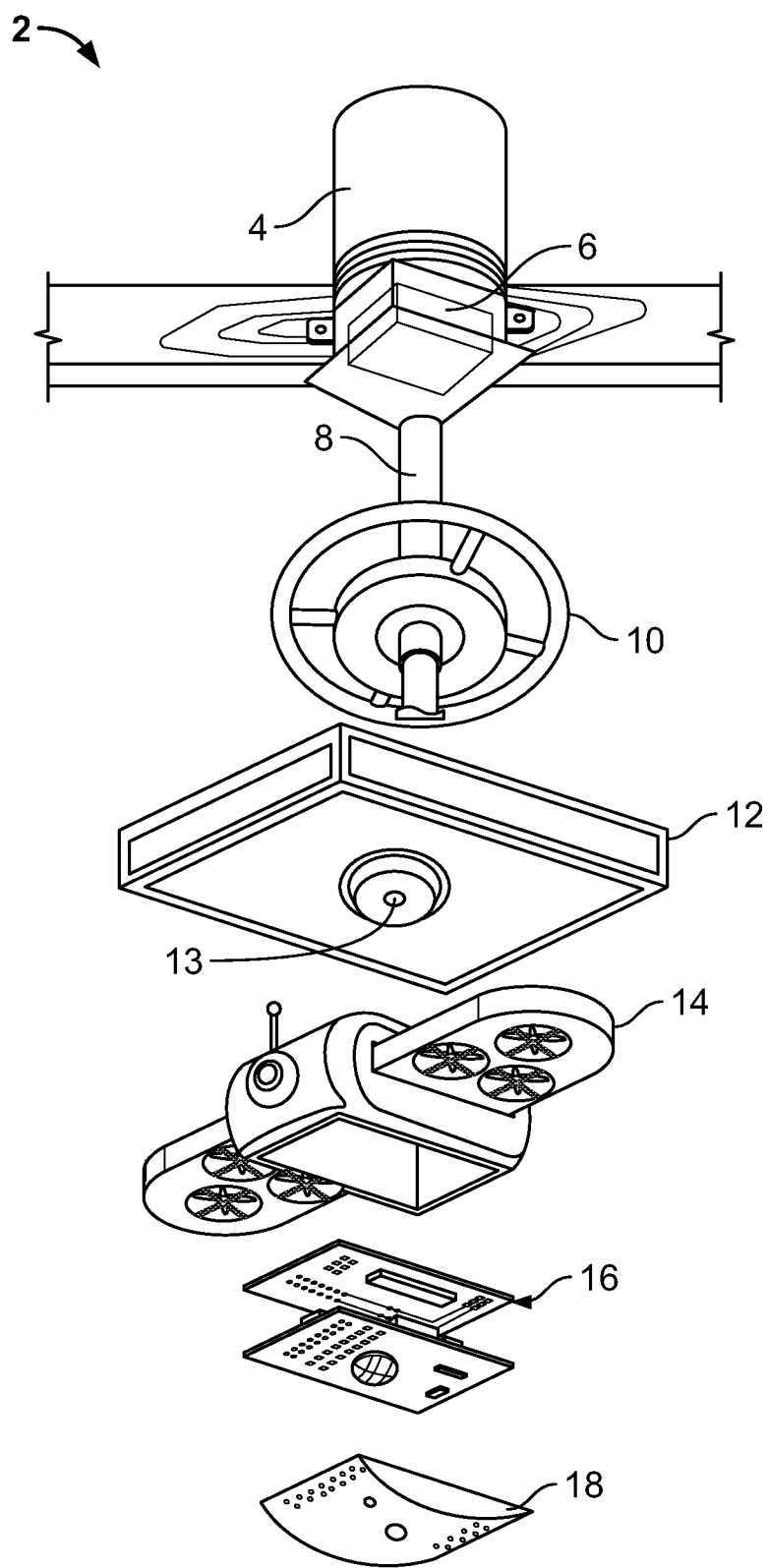
FIG. 1 is an exploded view of a first embodiment of an electrical fixture assembly of the present disclosure.

FIG. 1 is an exploded view of a first embodiment of an electrical assembly 2 of the present disclosure. The assembly 2 can include a rechargeable battery 4 located above a ceiling. The assembly 2 can also include a "sandbox" 6. The sandbox 6 is a universal adapter that allows a number of electrical components to be plugged into an electrical outlet. The sandbox 6 is described in U.S. patent application Ser. No. 13/972,883, published as United States Patent Application Publication No. 2014/0067137 and in U.S. patent application Ser. No. 14/693,600, published as United States Patent Application Publication No. 2016/0313744, both disclosures of which are hereby expressly incorporated by reference in their entireties. The sandbox 6 can be connected to the battery 4 or any other electrical power source. The assembly 2 can include a hydraulic titanium antenna lift 8. The lift 8 can be mechanically attached to the ceiling. The assembly 2 can also include a LED (light emitting diode) light 10 for illuminating a room. The light 10 can include a gap for accepting a shaft of the lift 8. The assembly 2 further includes a high-intensity narrow-spectrum ("HINS") light 12 for sanitizing a room. The HINS light 12 can have a violet hue for disinfection and sterilization. The light 12 can be attached to one of the lift 8. The assembly 2 can also include an attachment 13 for a drone 14. The attachment 13 can connect with a shaft of the antenna lift 8 which can be inserted through the LED light 10 as shown in FIG. 1. The drone 14 can include face-plate intelligence 16 and a wizard coordinator 18. Moreover, the drone can function as a ceiling fan by activating its propellers when the drone is docked. When fully assembled, the drone 14 can dock to the assembly 2 with the use of the attachment 13 on the HINS light 12. The drone 14 can receive power from the battery 4 or any other electrical source. Moreover, the assembly 2 can be adaptable to include a number of different devices, as explained in detail above. These devices include, but are not limited to, a load control device, coordinator device, security device, safety device, enhanced vision device, motion detection, biometric device, thermal detection device, daylight harvesting device, $CO_2$/Carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices.

Figure 2:
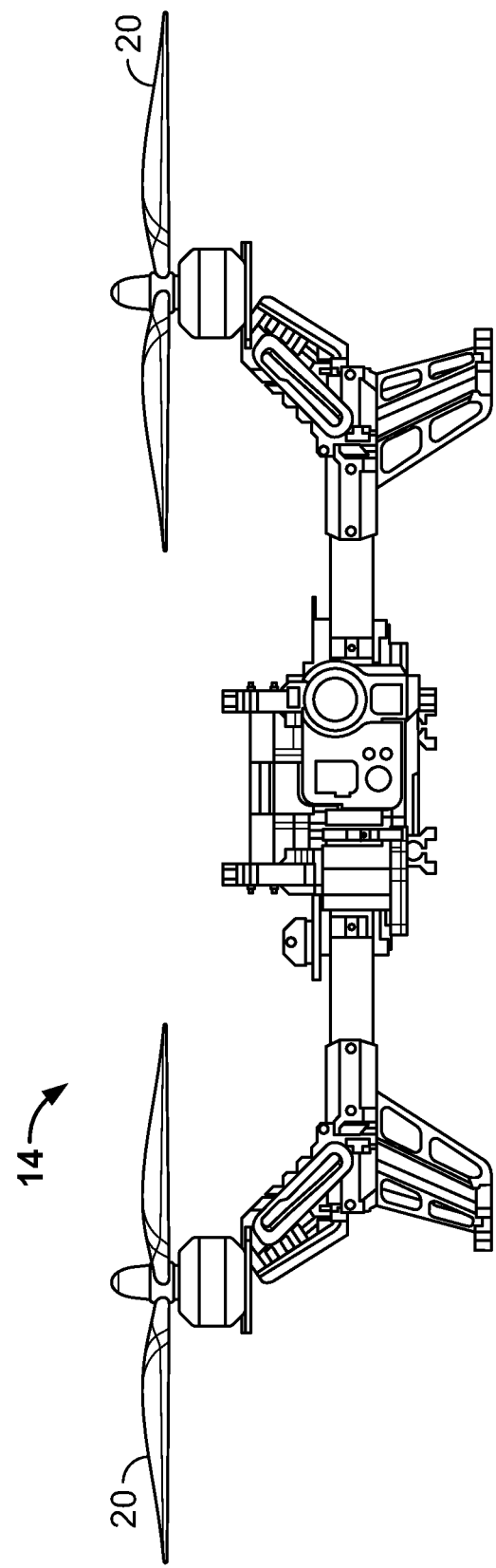
FIG. 2 is a front view of a drone of the present disclosure.
Figure 3:
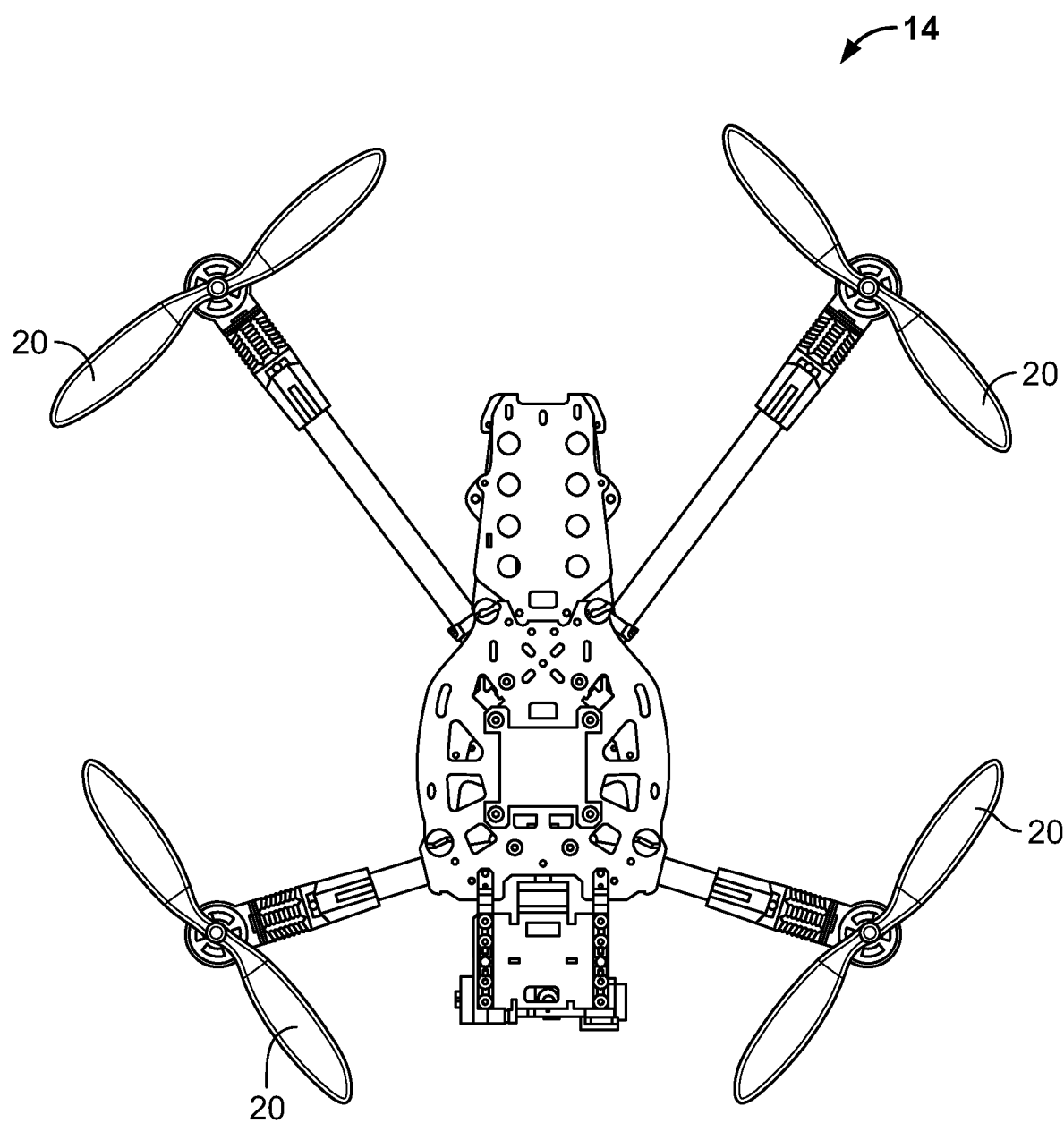
FIG. 3 is a bottom view of a drone of the present disclosure.

FIG. 2 is a front view of the drone 14 and FIG. 3 is a bottom view of the drone 14 shown in greater detail. As can be seen, the drone 14 can include a plurality of propellers 20. As explained above, the propellers 20 can provide a ceiling fan functionality as the propellers generate wind while mounted on the attachment 13.

Figure 4:
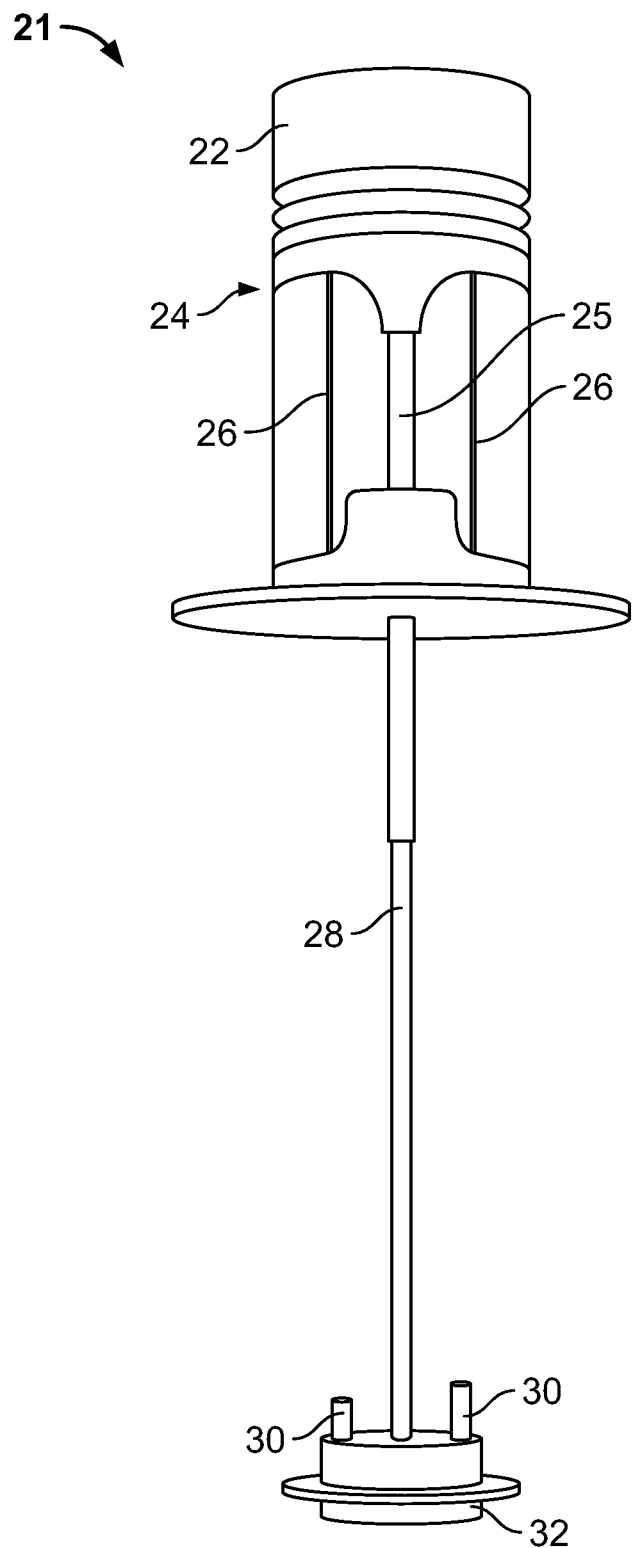
FIG. 4 is a perspective view of a second embodiment of an electrical fixture assembly of the present disclosure.

FIG. 4 is a perspective view of a second embodiment of an electrical fixture assembly 21 of the present disclosure. The assembly 21 includes a battery 22 and a hydraulic lift 24 connected to the battery 22. The lift 24 can adjust the assembly 21 vertically as desired. The lift 24 can include a shaft 25 extending downward and a plurality of wires 26 for assisting in adjusting the vertical position of assembly 21. The assembly 21 also includes a titanium antenna extender 28 mechanically secured to the lift 24 via the shaft 25. The assembly 21 also includes prongs 30 on an LED light 32. Moreover, the assembly 21 can be adaptable to include a number of different devices, as explained in detail above. These devices include, but are not limited to, a load control device, coordinator device, security device, safety device, enhanced vision device, motion detection, biometric device, thermal detection device, daylight harvesting device, $CO_2$/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices.

Figure 5:
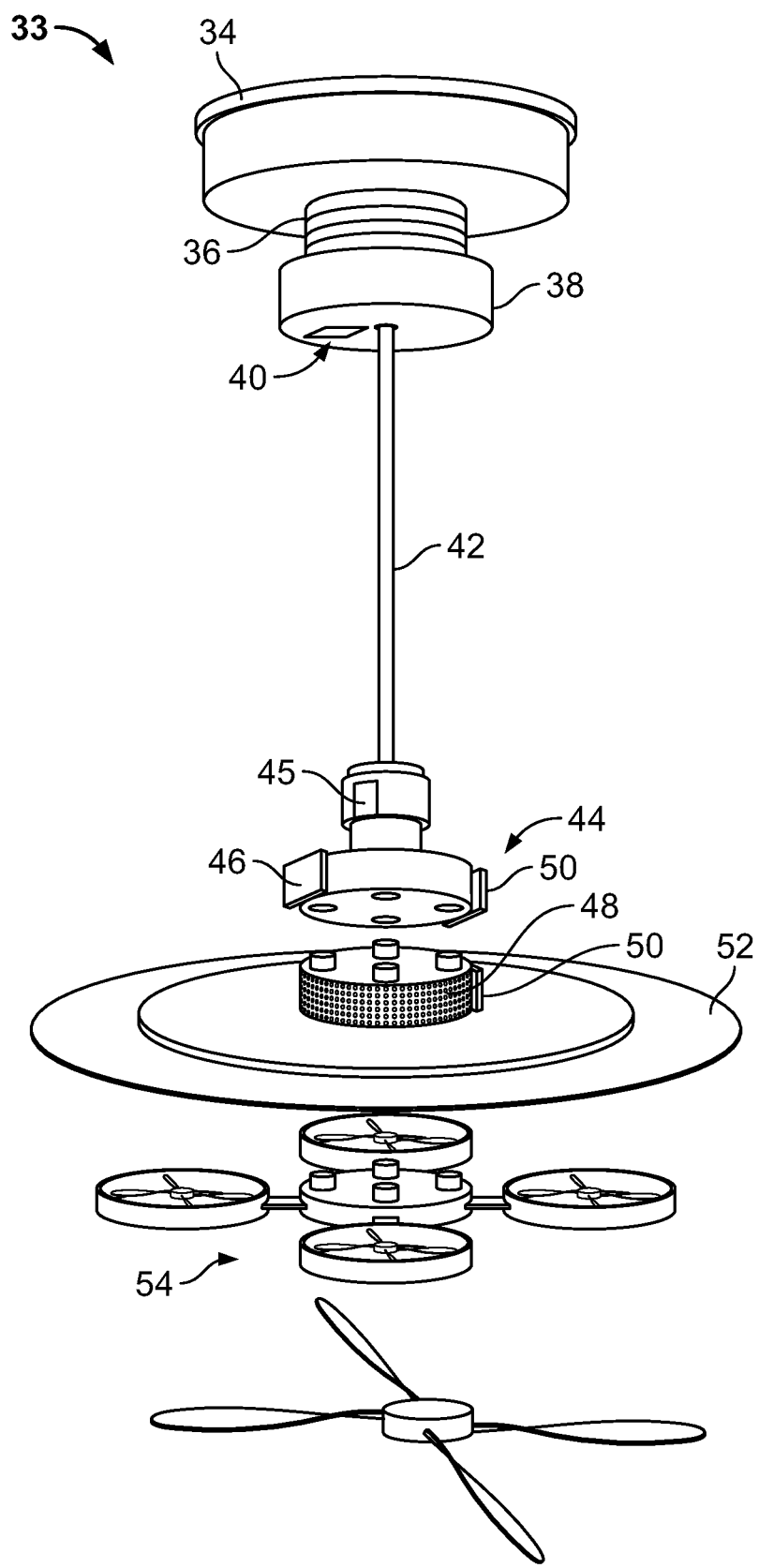
FIG. 5 is a perspective view of a third embodiment of an electrical fixture assembly of the present disclosure.

FIG. 5 is a perspective view of a third embodiment of an electrical fixture assembly 33 of the present disclosure. The assembly 33 includes a battery 34. Any alternative power source can be used in the present disclosure. Connected to the battery 34 is a hydraulic lift 36 for moving the assembly 33 in the vertical direction. The assembly 33 further includes an electrical box 38 for housing various electrical components or electrical power sources. The electrical box 38 includes a sandbox 40. As explained in greater detail above, the sandbox 40 is a universal adapter that allows a number of electrical components to be plugged into an electrical outlet. A titanium antenna extender 42 can be mechanically attached to and is in mechanical communication with the lift 36. The other end of the titanium antenna extender 42 can be mechanically fastened to a smoke detector 44. The smoke detector 44 can detect smoke. Optionally, other detectors can be used such as a motion detector. The smoke detector 44 can include a coordinator for proving coordination functionality. Moreover, the smoke detector 44 can include a load control 46 for controlling the load of the assembly 33. The smoke detector 44 can be attached to a microphone 48 for transmitting audio messages. The microphone 48 and the smoke detector 44 can include devices 50 for providing the ability of the assembly 33 to further integrate with other devices or providing power to the current devices. The assembly 33 can further include an LED glass light 52 for providing illumination. As mentioned above, a HINS could also be provided in this arrangement. The assembly 33 can include a drone 54 attached to the bottom end of the microphone 48. The drone 54 can optionally be directly attached to the smoke detector 44 if the microphone 48 is not desired. Moreover, the assembly 33 can be adaptable to include a number of different devices, as explained in detail above. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices.

Figure 6:
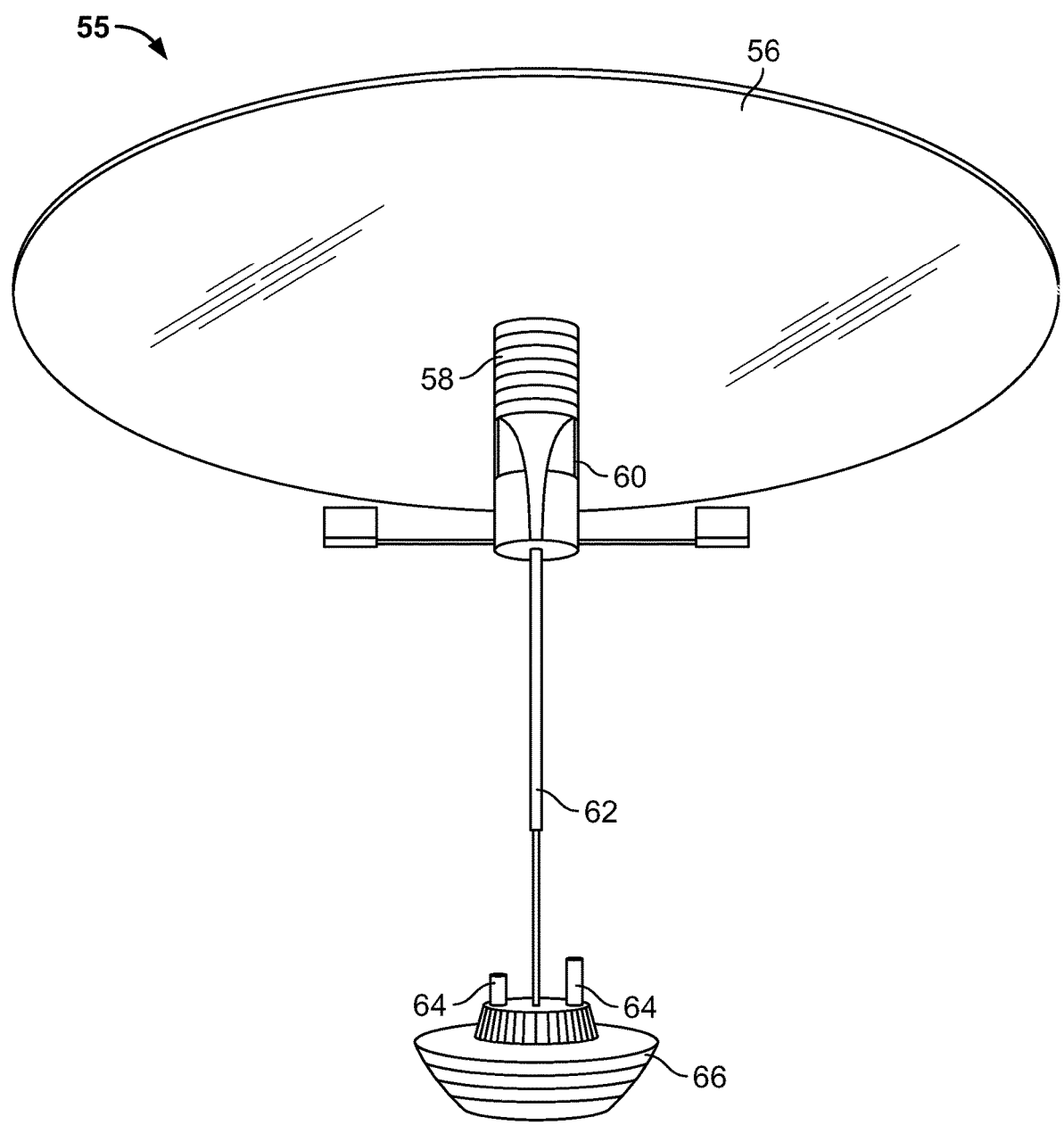
FIG. 6 is a perspective view of a fourth embodiment of an electrical fixture assembly of the present disclosure.

FIG. 6 is a perspective view of a fourth embodiment of an electrical fixture assembly 55 of the present disclosure. The assembly 55 can include a mirror 56 hanging on a ceiling or a wall. A battery 58 can be attached to the mirror 56. A hydraulic lift 60 can be attached to the battery 58 for moving the assembly 55 in a vertical direction. The assembly 55 also includes a titanium antenna extender 62 which can be mechanically secured to the hydraulic lift 60. As the hydraulic lift 60 moves the assembly 55 in a vertical direction, the extender 62 correspondingly moves in a vertical direction. The assembly 55 includes a plurality of prongs 64 for receiving and attached a device to the assembly 55. The assembly 55 further includes a torchlight fixture 66. The fixture 66 can also be any other lighting fixture known in the art. Moreover, the assembly 55 can be adaptable to include a number of different devices, as explained in detail above. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices.

Figure 7:
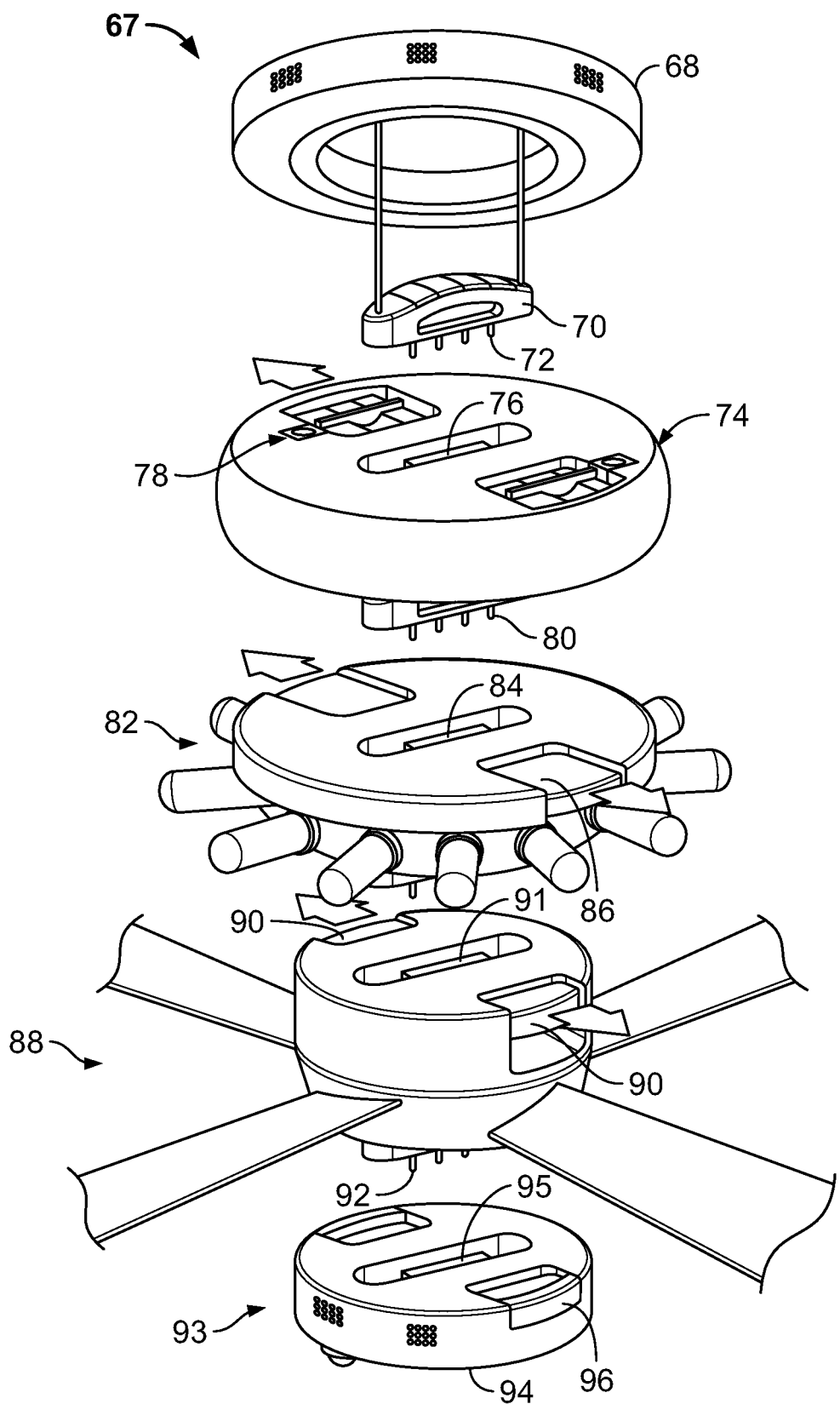
FIG. 7 is an exploded view of a fifth embodiment of an electrical fixture assembly of the present disclosure.

FIG. 7 is an exploded view of a fifth embodiment of an electrical fixture assembly 67 of the present disclosure. The assembly 67 includes a top member 68 which can be attached to a ceiling or a wall. The top member 68 can include ceiling contacts 70 having a plurality of pins 72. The assembly 67 can include a device 74. The assembly 67 can be adaptable to include a number of different devices, as explained in detail above. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices. In the example embodiment of FIG. 7, device 74 can be a smoke detector. The device 74 can having a latch 76 for mechanical attachment to the plurality of pins 72. The device 74 can further include a lock option 78 for locking the device 74 in place with the top member 68. The device 74 can further include on the bottom a bottom member having a plurality of pins for attaching another device. The device can be any of the devices mentioned above. In the example embodiment of FIG. 7, an LED light 82 can be attached to the device. The LED light 82 can include a latch 84 for attaching the LED light 82 to the device 74 via the plurality of pins 80. The LED light 82 can include a switch 86 for releasing the LED light 82 from the device 74 by activating the latch 84. The LED light 82 can further include a bottom member having a plurality of pins for attaching another device. The device can be any of the devices mentioned above. In the example embodiment of FIG. 7, a fan 88 can be attached to the LED light 82 via the latch 91. The fan 88 can include a switch 90 for disengaging the latch 91 from plurality of pins of the LED light 82 and thus removing the fan 88 from the LED light 82. The fan 88 can include a bottom member with a plurality of pins 92 for attaching another device. The device can include any of the devices mentioned above. In the example embodiment of FIG. 7, a coordinator camera/microphone/speaker 93 can be attached to the fan 88 via the latch 95 being attached to the plurality of pins 92. The coordinator camera/microphone/speaker 93 can include a center magnetic drone mount 94 for receiving a drone. The coordinator camera microphone speaker 93 can also include a switch 96 for removing the coordinator camera microphone speaker 93 from the fan 88 by disengaging the latch 95 from the plurality of pins 92.

Figure 8:
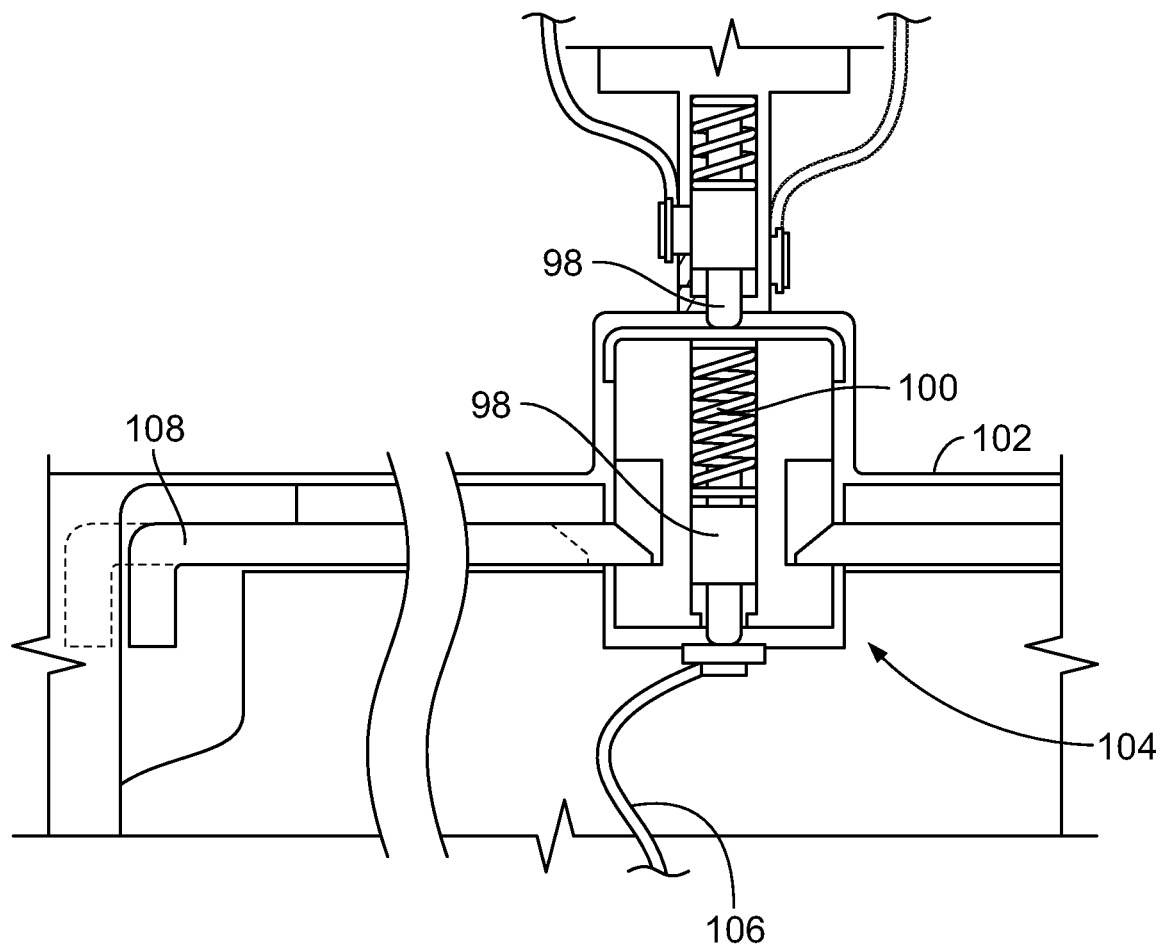
FIG. 8 is a cross-sectional view of the fifth embodiment of the present disclosure.

FIG. 8 is a cross-sectional view of the fifth embodiment of a portion of the assembly 67. As can be seen a plurality of spring contacts 98 engage a spring 100 for securing a device to a ceiling 102 or securing a device to another device. This arrangement allows a top module 104 to have electrical wiring 106 move through the assembly 67, from the power source to further device or module. As the spring 98 engages a latch on a device a member 108 can be moved in the horizontal direction to allow for engaging and disengaging of the spring contact 98 to remove the devices from each other.

Figure 9:
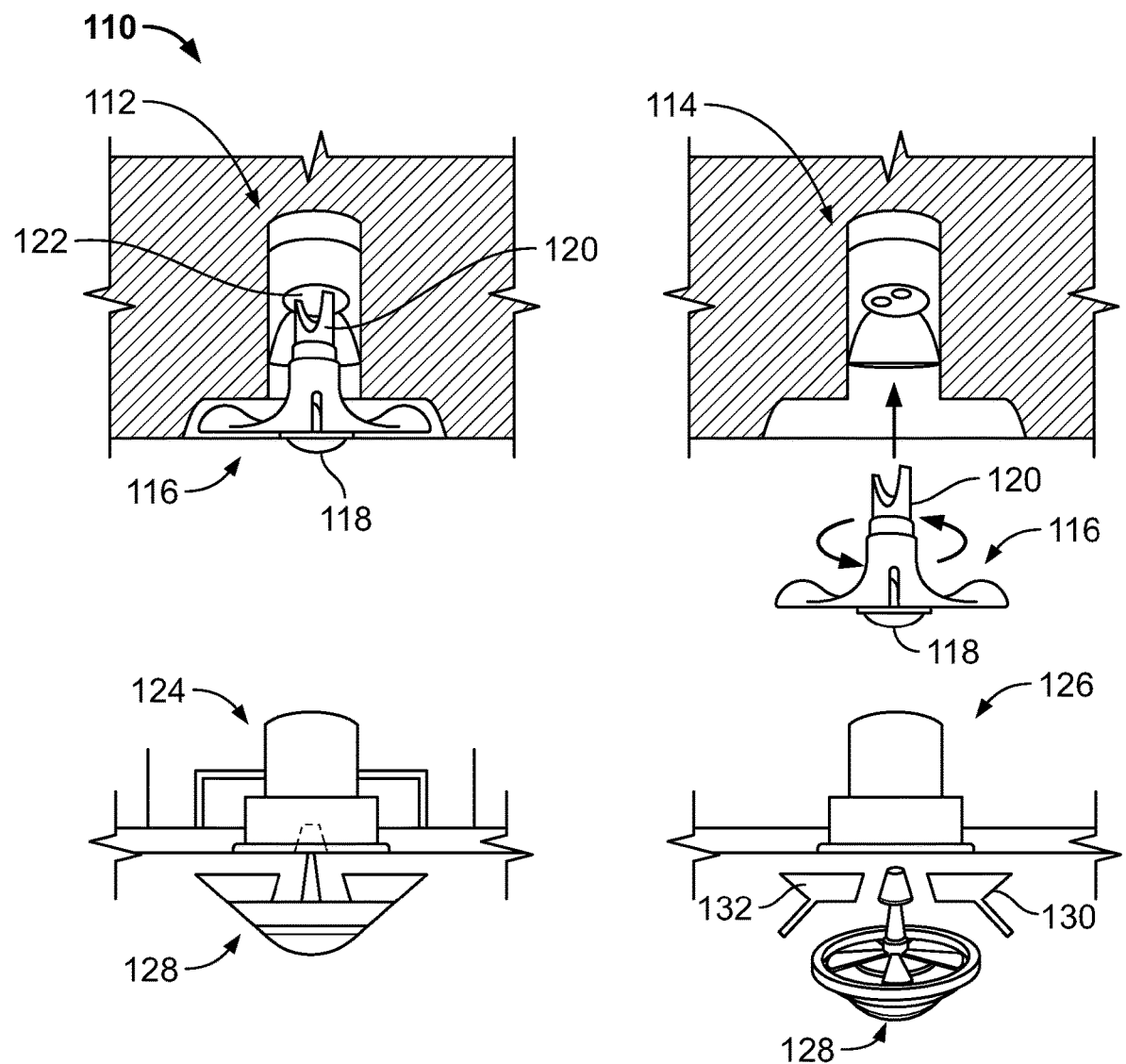
FIG. 9 is a diagram of a sixth embodiment of an electrical fixture assembly of the present disclosure.

FIG. 9 is a diagram of a sixth embodiment of an electrical fixture assembly 110 of the present disclosure. The assembly 110 includes a recess 112 which can be located in a ceiling for receiving a drone 116. The drone 116 can include a light 118 for illuminating a room. The drone 122 can further include a connector 122 for mechanically fastening the drone 116 to the recess 112. The drone 116 can rotate in a circular fashion and thread into a threaded mating connection in the recess 112. Alternatively, the mechanical connection can be snap-fit or any other suitable mechanism. The drone 116 can release itself from the recess 112 and move to another recess 114 where light may be needed. A central processor can track the movement of an individual and remotely move the drone 116 to another location to provide light wherever necessary. There can be multiple drones functioning within a system of recesses as well. For example drone 128 can attach to recess 124 and move to recess 126 where light is needed. If the recess 126 is of a different arrangement, the drone can change its shape such as by removing side members 130 and 132.

Figure 10:
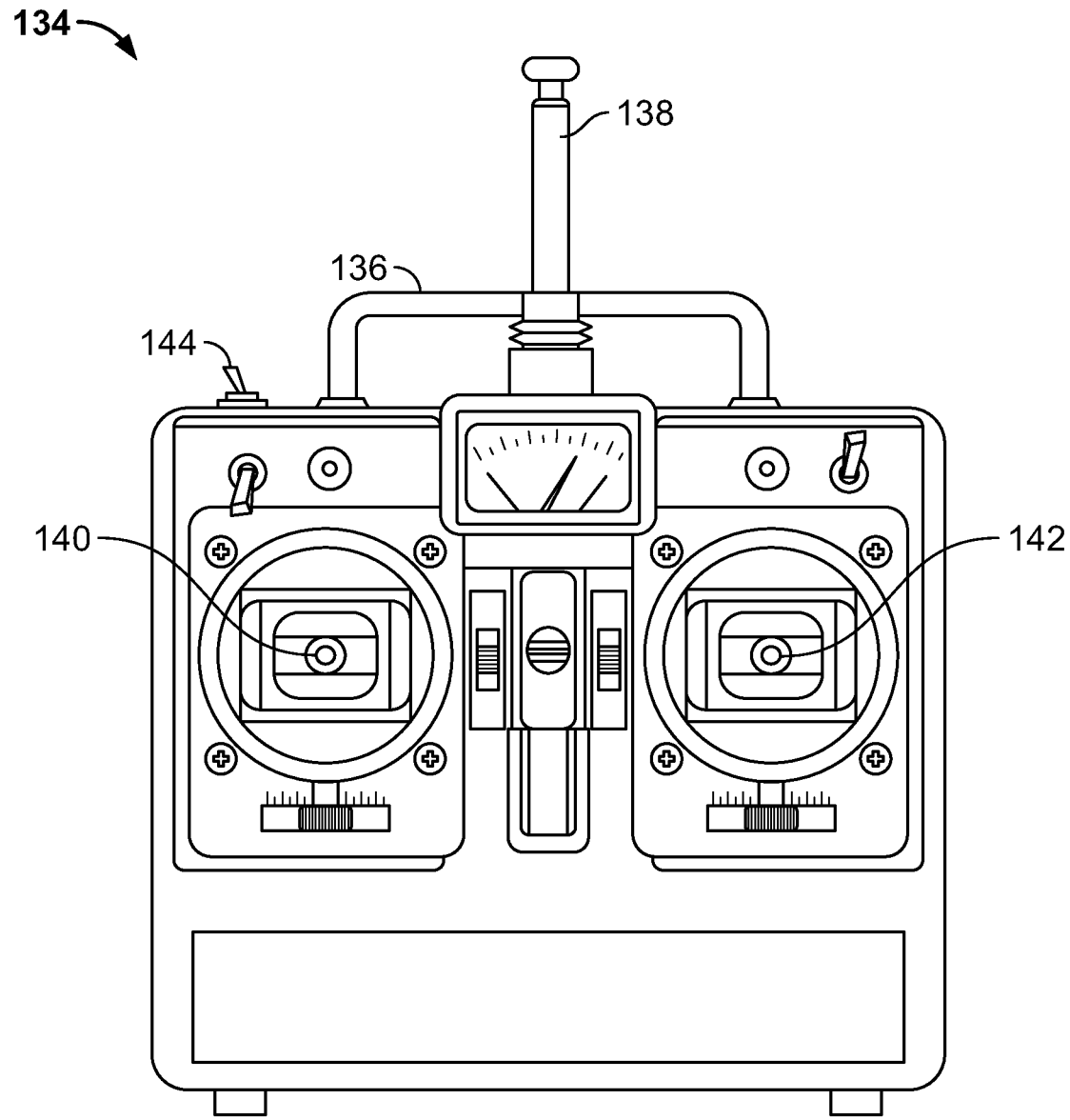
FIG. 10 is a front view of a first embodiment of a controller of the present disclosure.

FIG. 10 is a front view of a first embodiment of a controller 134 for controlling a drone in FIG. 9. The controller 134 can include a handle 136 and an antenna 138. The controller 134 can include a first control 140 and a second control 142 for moving a drone in a desired direction. The controller 134 can further include a landing switch 144 for assisting the drone in landing.

Figure 11:
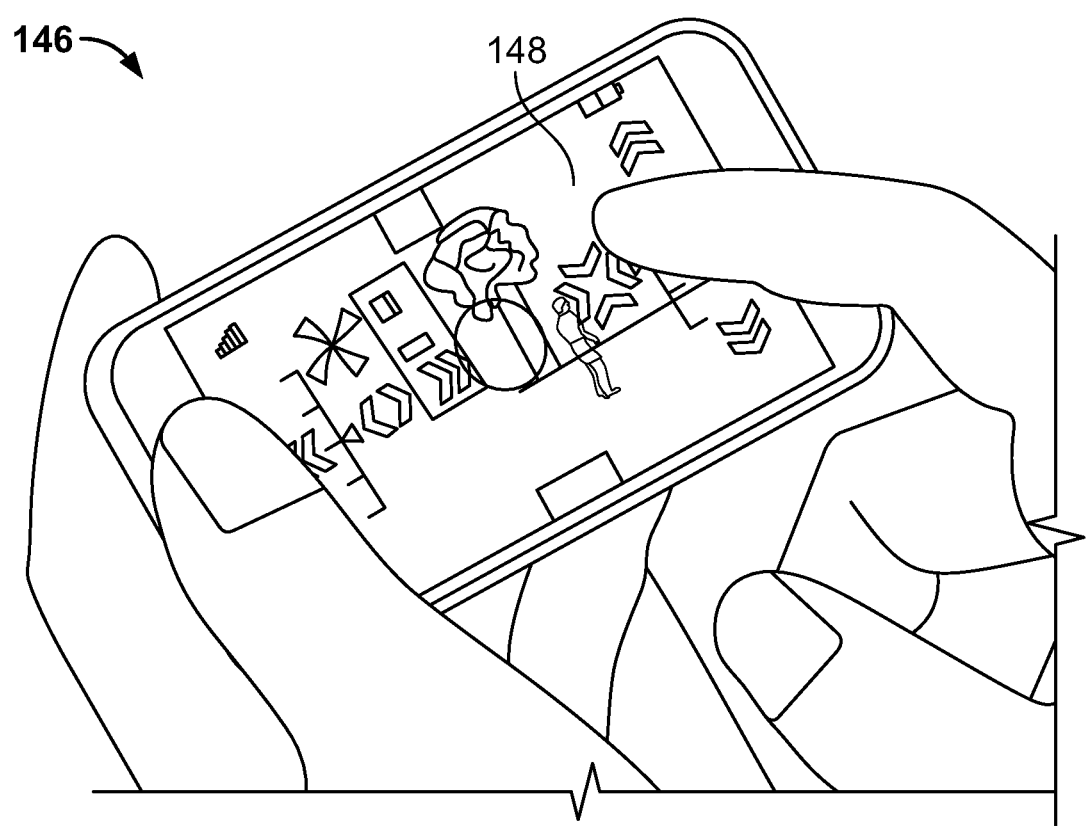
FIG. 11 is a perspective view of a second embodiment of a controller of the present disclosure.

FIG. 11 is a perspective view of a second embodiment of a controller 146 for controlling a drone in FIG. 9. The controller 146 can be a smartphone or any other suitable mobile device. The controller 148 can include a touch screen showing live video of a camera on the drone. Alternatively, the controller 148 can show a user interface for controlling the movement of the drone. A split screen can be also be shown to provide the user with a live view and the controls.

Figure 12:
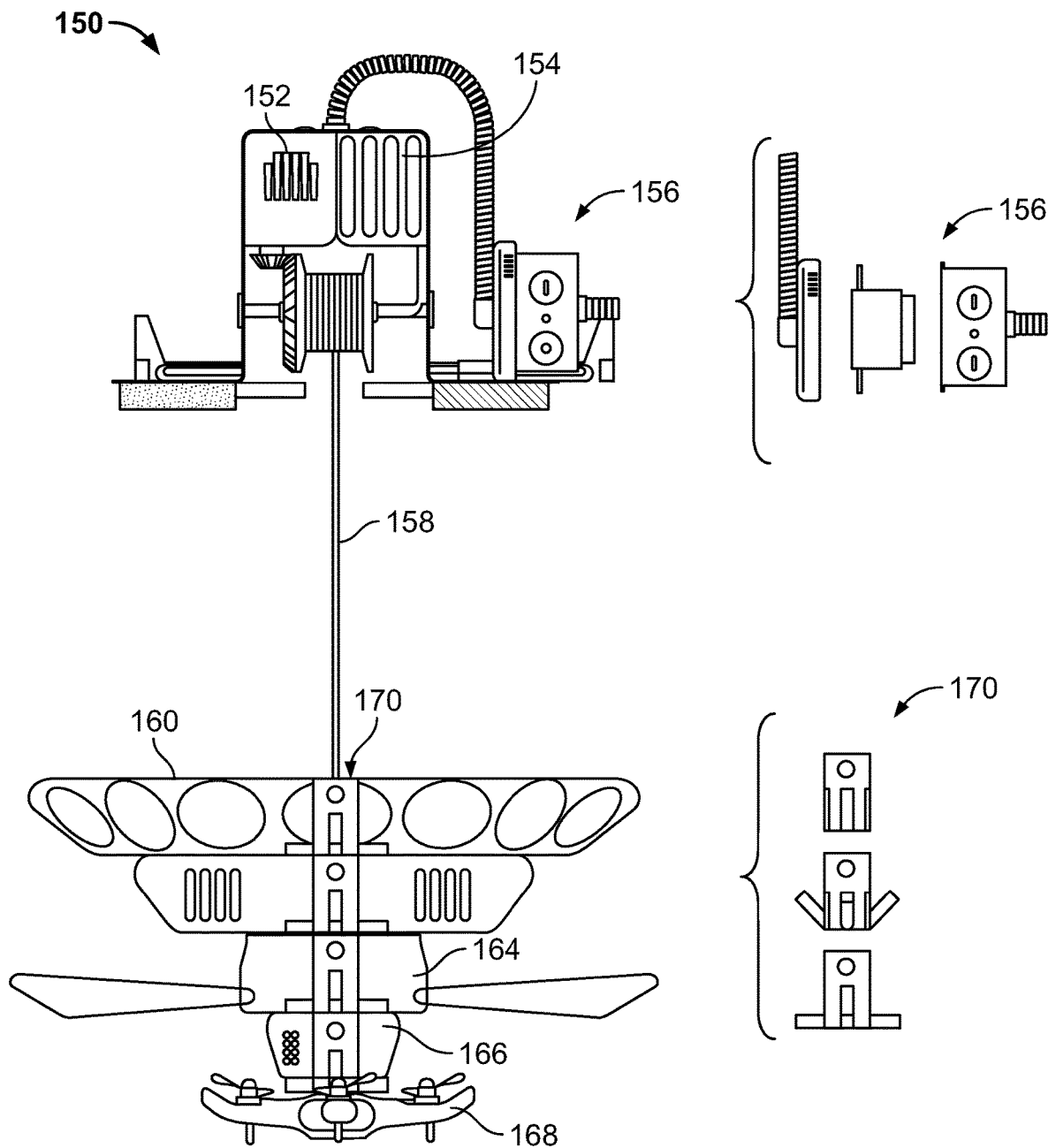
FIG. 12 is a perspective view of a seventh embodiment of an electrical fixture assembly of the present disclosure.

FIG. 12 is a perspective view of a seventh embodiment of an electrical fixture assembly 150 of the present disclosure. The assembly includes a motor 150 in electrical communication with a battery 154. An alternative power source can be used with the present disclosure. The motor 152 and battery 154 can be mechanically fastened to a super conduit 156 for securing the assembly 150. The assembly 150 can include a cable 158 which can vertically extend down from the ceiling for attaching a plurality of device as will be explained in greater detail below. The cable 158 can move vertically via a power source. The assembly 150 can be adaptable to include a number of different devices, as explained in detail above. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices. In the example embodiment of FIG. 12, the assembly 150 includes a UVC disinfection device 160, a coordinator 162, a fan 164, a speaker/microphone 166, and a drone 168. All of these devices are mechanically fastened with a "superstack" 170. The superstack 170 can be hot shoe device connectors for mechanically securing a plurality of devices. The drone 168 can be removably attached to the assembly 150 to perform other functions in other places.

Figure 13:
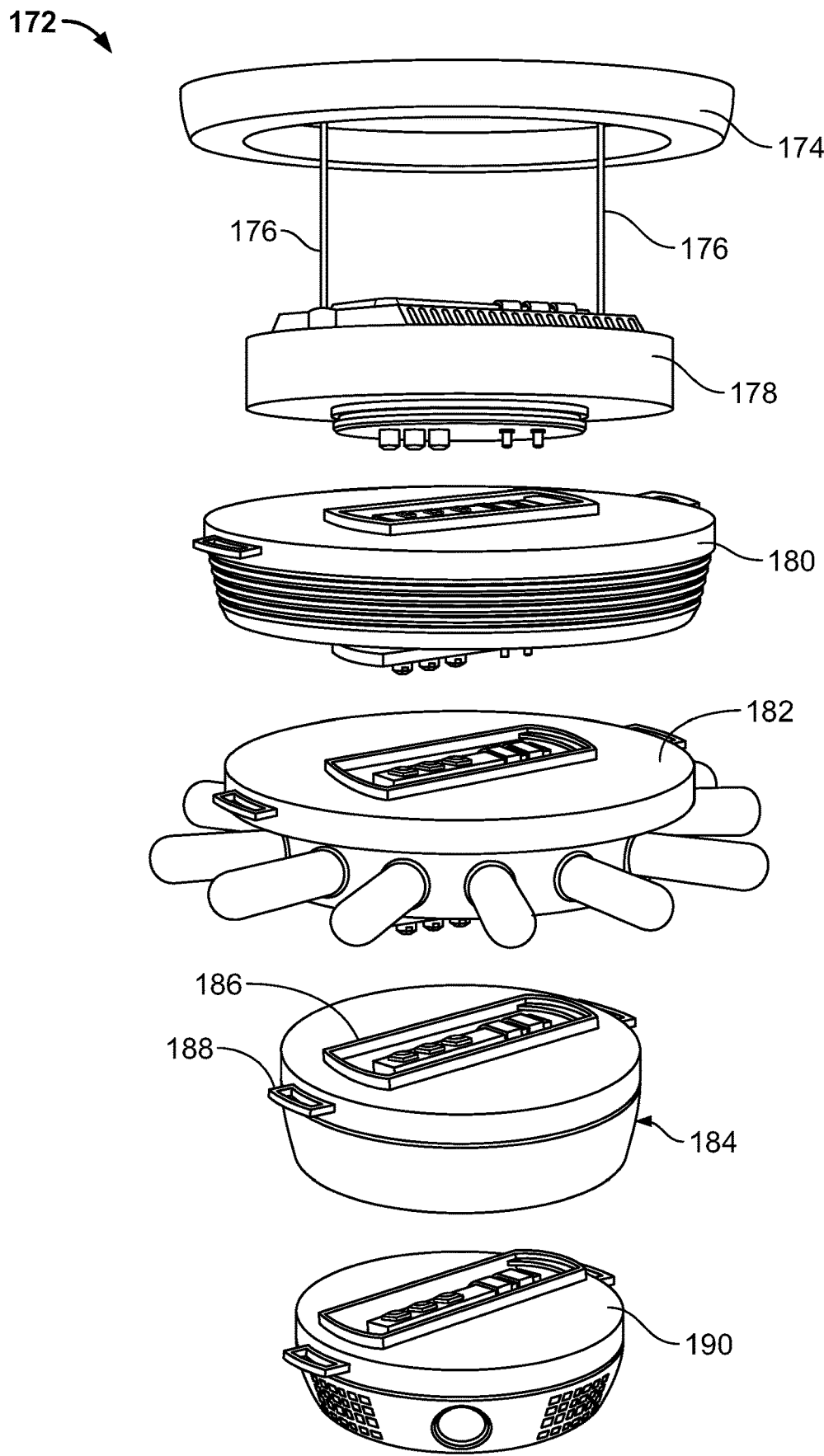
FIG. 13 is a perspective view of an eight embodiment of an electrical fixture assembly of the present disclosure.

FIG. 13 is a perspective view of an eight embodiment of an electrical fixture assembly 172 of the present disclosure. The assembly 172 includes a fixture 174 being attached to a ceiling or a wall. The fixture 174 can include a plurality of cables 176 having reels for moving the cables 176 and the assembly 172 in a vertical direction. The assembly 172 can include a device 178 which can be attached to the cables 176. The device 178 can take alternating current as input and output direct current. The device 178 can also be a battery, a sandbox (as explained in greater detail above with relevant disclosures incorporated by reference), and/or a load controller. The device 178 can also have a plurality of RJ-45 connections. The assembly 172 can include an air cleaner 180 which can be attached to the device 178. The assembly 172 can also include a UVC light 182 attached to the air cleaner 180 for disinfection functions. The assembly 172 can also include an LED light 184. The LED light 184 can include a module attachment 186 for mechanically attaching to the UVC light 182. A plurality of other devices can also be compatible with the module attachment 186. The LED light 184 can also include a release mechanism 188 for disengaging the LED light 184 from the UVC light 182. The assembly 172 can also include a smoke detector 190 for attaching to the LED light 184. The smoke detector 190 can also have a microphone, camera and speaker. Any of the devices in this embodiment can be substituted for any other device as described in the present disclosure. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices.

Figure 14:
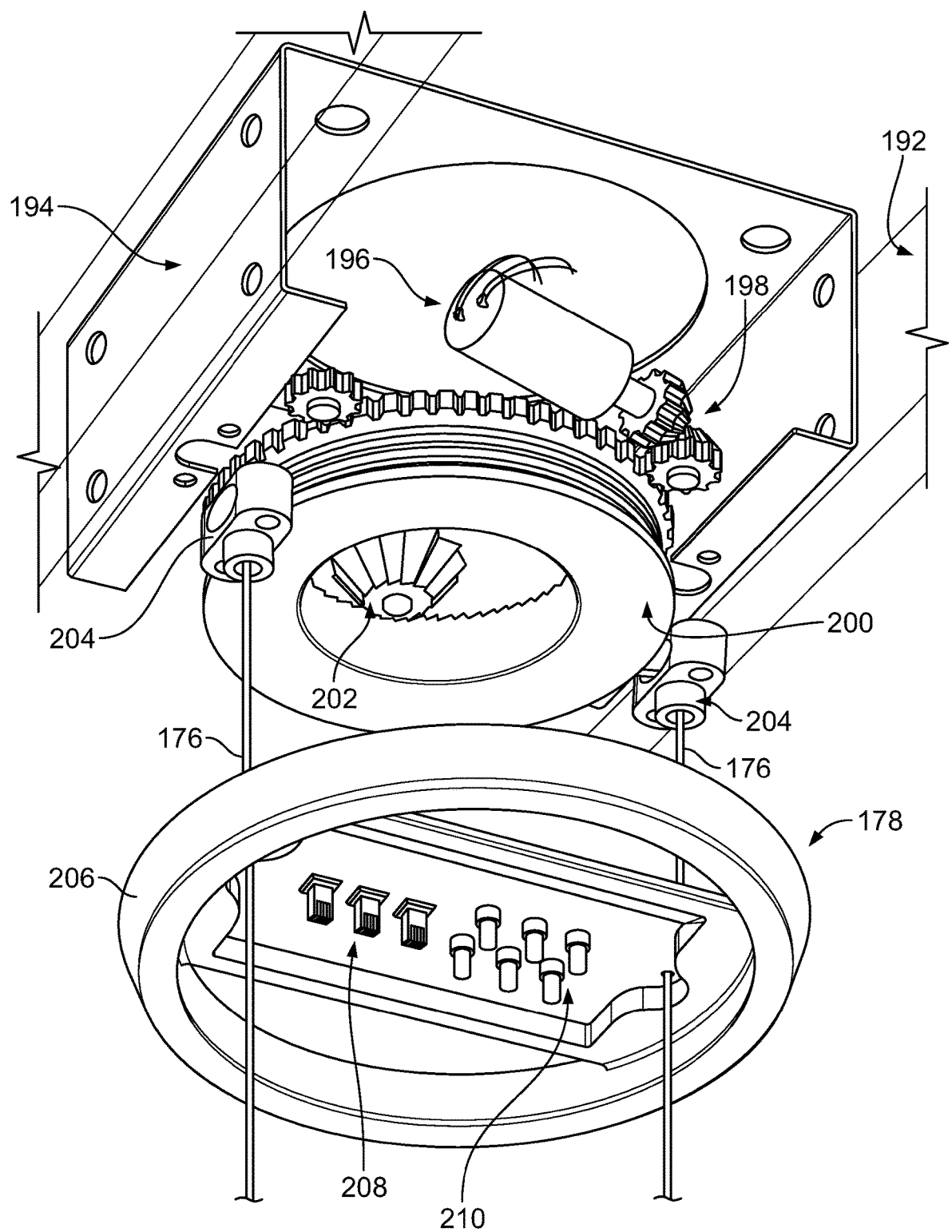
FIG. 14 is a perspective view showing portions of the electrical fixture assembly of FIG. 13 in greater detail.
Figure 14A:
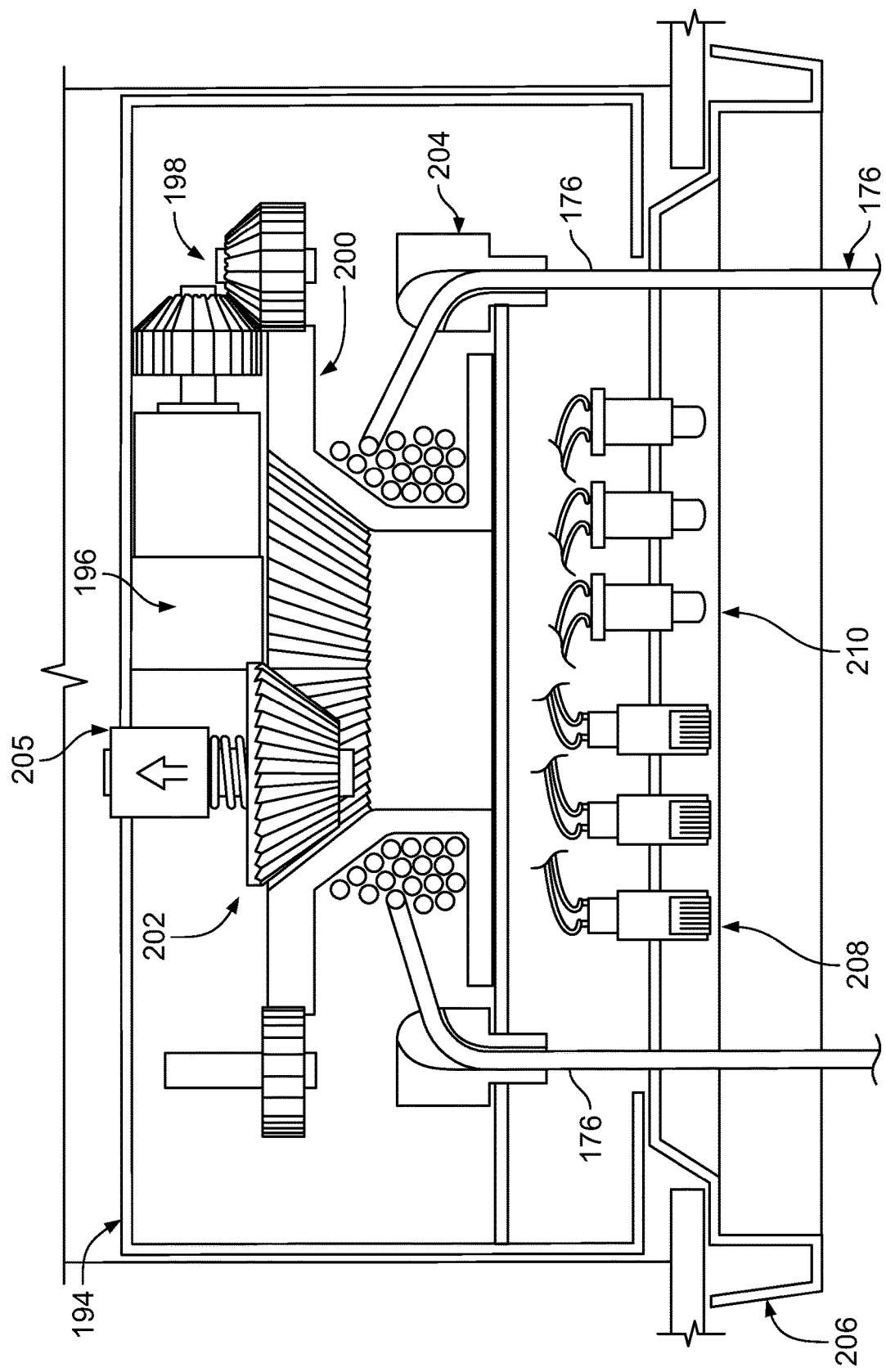
FIG. 14A is a cross-sectional view of FIG. 14 showing portions of the electrical fixture assembly of FIG. 13 in greater detail.

FIG. 14 is a perspective view showing the device 178 and fixture 174 of FIG. 13 in greater detail and FIG. 14A is a cross-sectional view of the device 178 and fixture 174. The assembly 172 can be mounted on a joist 192 by using a mounting bracket 194. The assembly 172 includes a cable drive motor 196 for generating electrical power to a gear drive 198. The gear drive 198 is in mechanical communication with a cable reel 200 which both rotate as the motor 196 provides electrical power. The anti-reversing ratchet gear 202 is also in mechanical communication with the cable reel 200 for moving the cables 176 in a vertical direction. The assembly 172 also includes a cable feeder 204 housing the cables 176. Moreover, a disengaging solenoid 205 is provided which moves in the upward direction to engage or disengage the ant-reversing ratchet gear 202. FIG. 14 also shows the device 178 in greater detail. As can been seen a fascia can house the device 178. The device 178 can include a plurality of RJ-45 connections 208 and a plurality of power out spring pins 210 for electrical communication with another device attached thereto.

Figure 15:
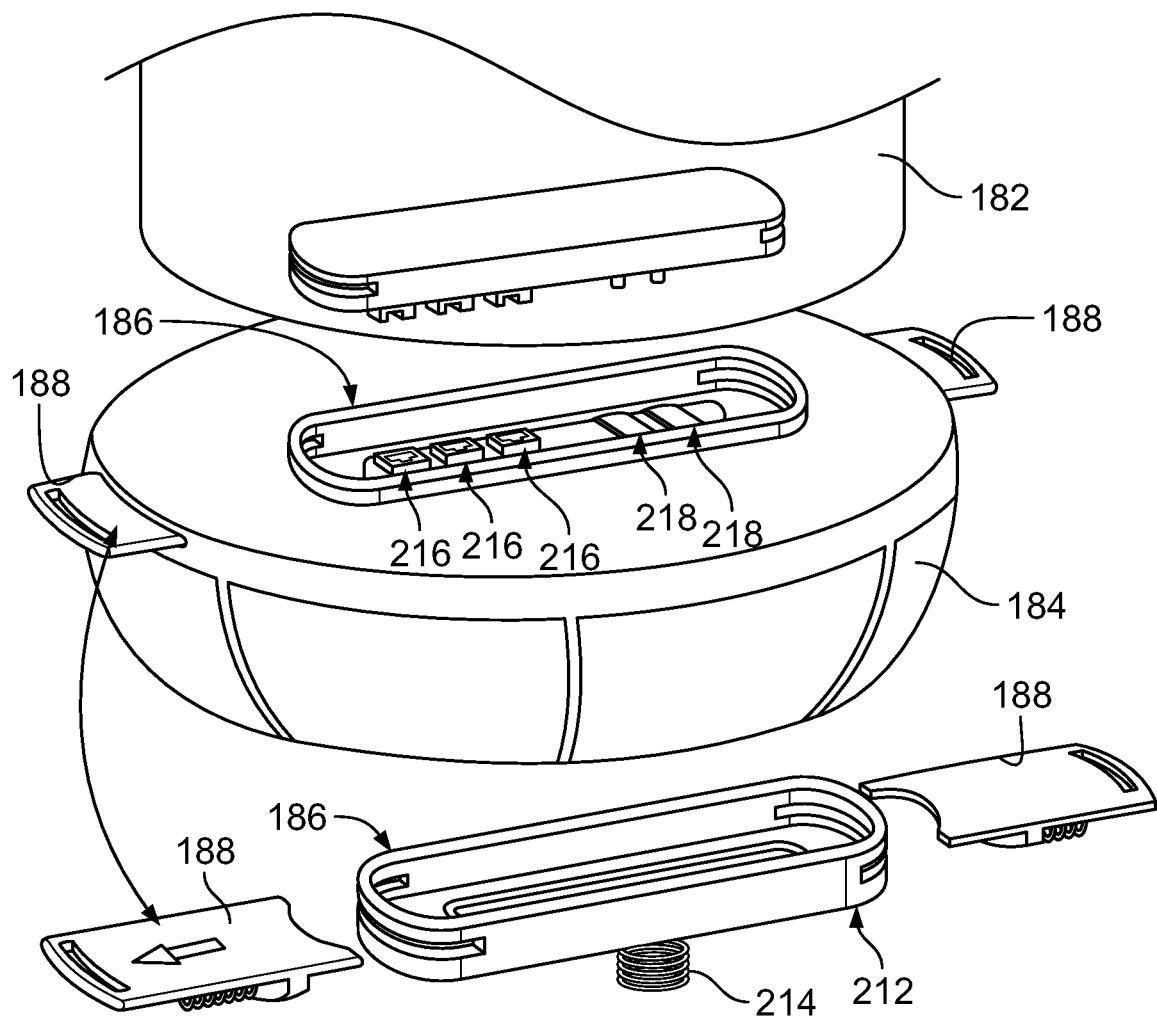
FIG. 15 is a perspective view showing the button-latch mechanism of FIG. 13 in greater detail.

FIG. 15 is a perspective view showing the button-latch mechanism of FIG. 13 in greater detail. In particular, the module attachment 186 includes a center adapter 212 and spring 214. The center adapter 212 houses a plurality of RJ-45 connections 216 and a plurality of DC power connections 218. The plurality of RJ-45 connections 216 and the plurality of DC power connections 218 can connect with the corresponding connections on another device, such as UVC light 182 in the example of FIG. 13.

Figure 16:
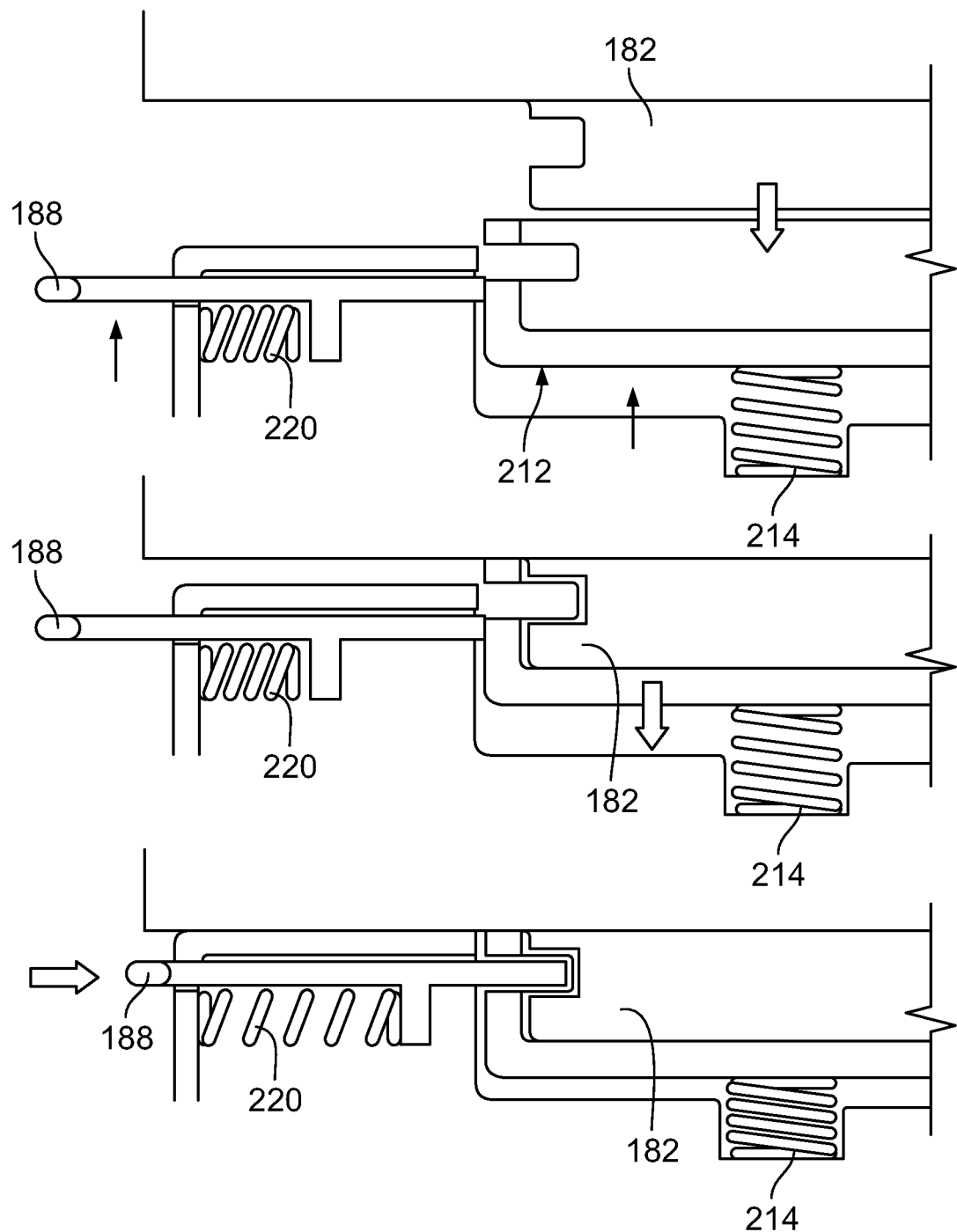
FIG. 16 is a cross-sectional view showing the button-latch mechanism of FIG. 15.

FIG. 16 is a cross-sectional view showing the button-latch mechanism in greater detail. In particular, and for illustrative purposes only, as UVC light 182 is pushed downward on the LED light 184, the spring 214 can compress. As the spring 214 compresses, the spring 220 can also compress. Once the UVC light 182 is fully pushed, the release mechanism 188 can snap into a groove which allows the spring 220 to decompress. The mechanism 188 can be pulled outward which would allow the UVC light 182 to be removed from the mechanism. This same mechanism can be used with all the devices described in the present disclosure. For example, the device 178 can be connected to the air cleaner 180 via the button-latch mechanism.

Figure 17:
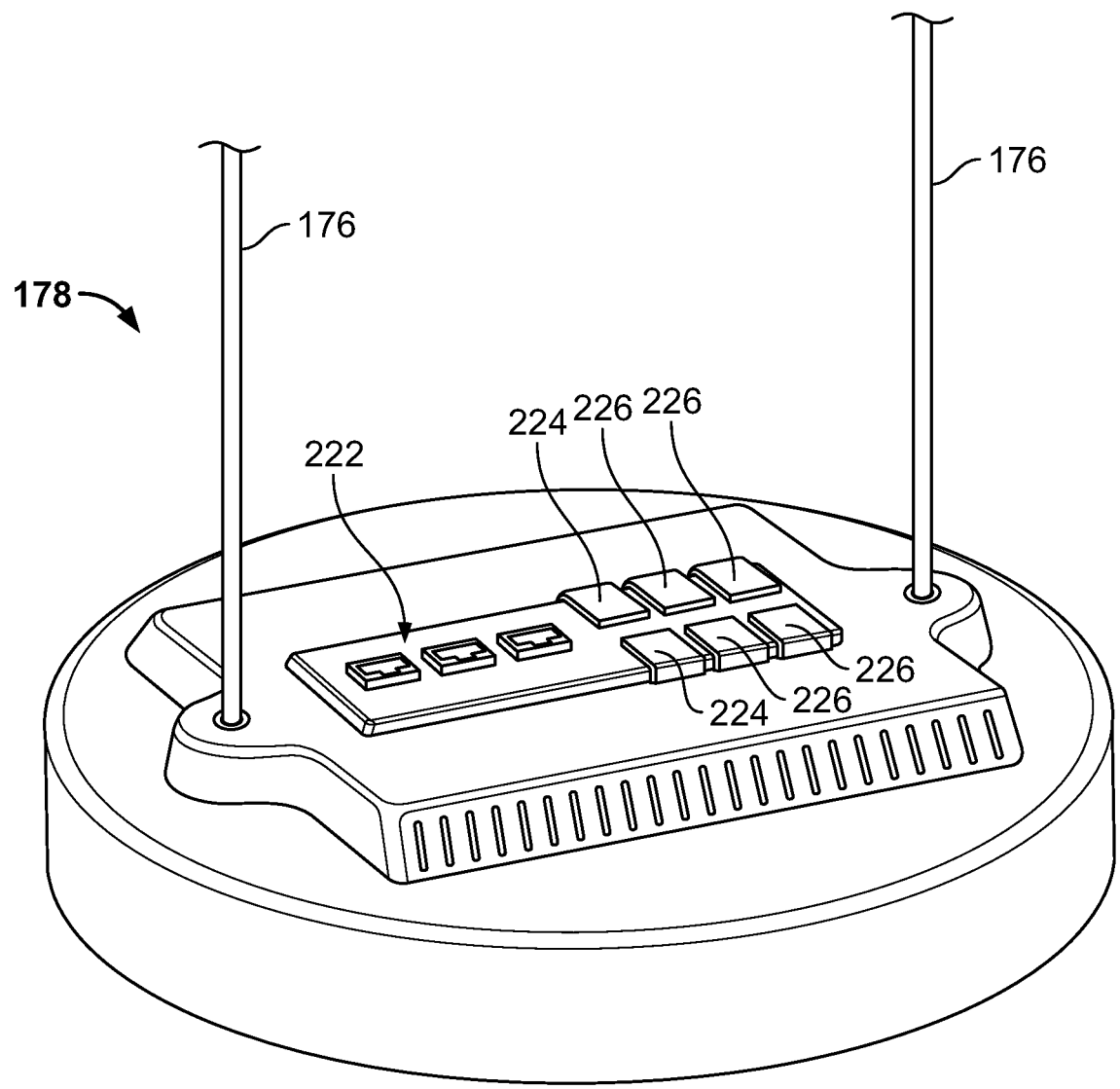
FIG. 17 is a perspective view of the device of FIG. 13 shown in greater detail.

FIG. 17 is a perspective view of the device 178 of FIG. 13 shown in greater detail. The device 178 includes a plurality of RJ45 connectors 222, a plurality of AC contacts 224 and a plurality of DC contacts 226.

Figure 18:
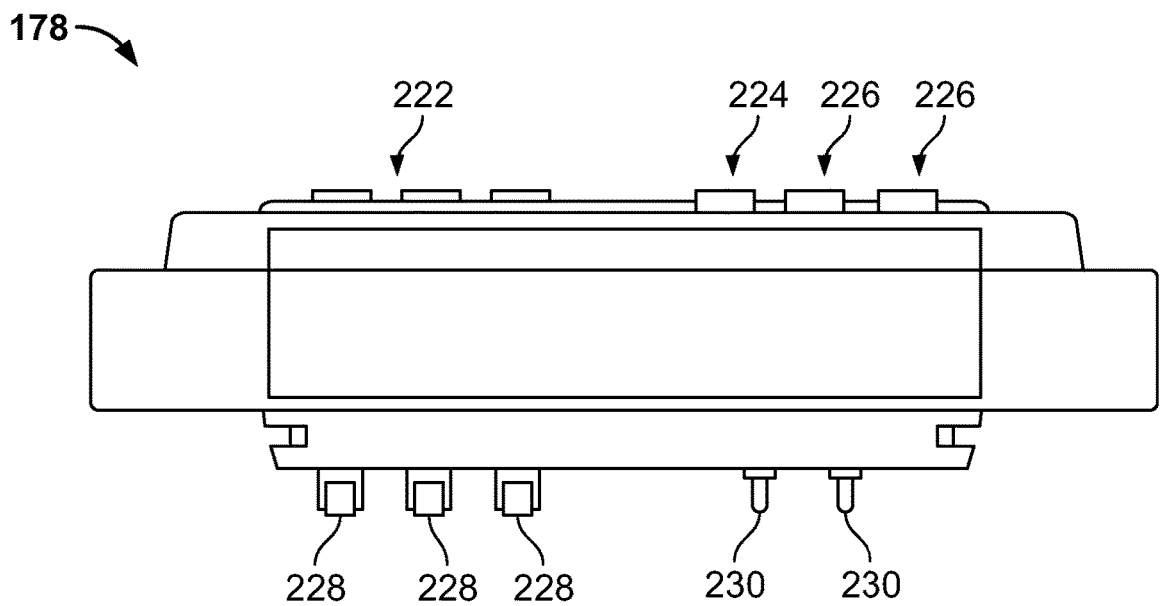
FIG. 18 is a side view of the device of FIG. 13 shown in greater detail.

FIG. 18 is a side view of the device 178 of FIG. 13 shown in greater detail. The device 178 further includes a plurality of RJ-45 out connections 228 and a plurality of DC power out connections 230. Referring back to FIG. 13, these the plurality of RJ-45 out connections 228 and the plurality of DC power out connections 230 would provide electrical signals to the air cleaner 180 or any other device that may be substituted in the assembly 172.

Figure 19:
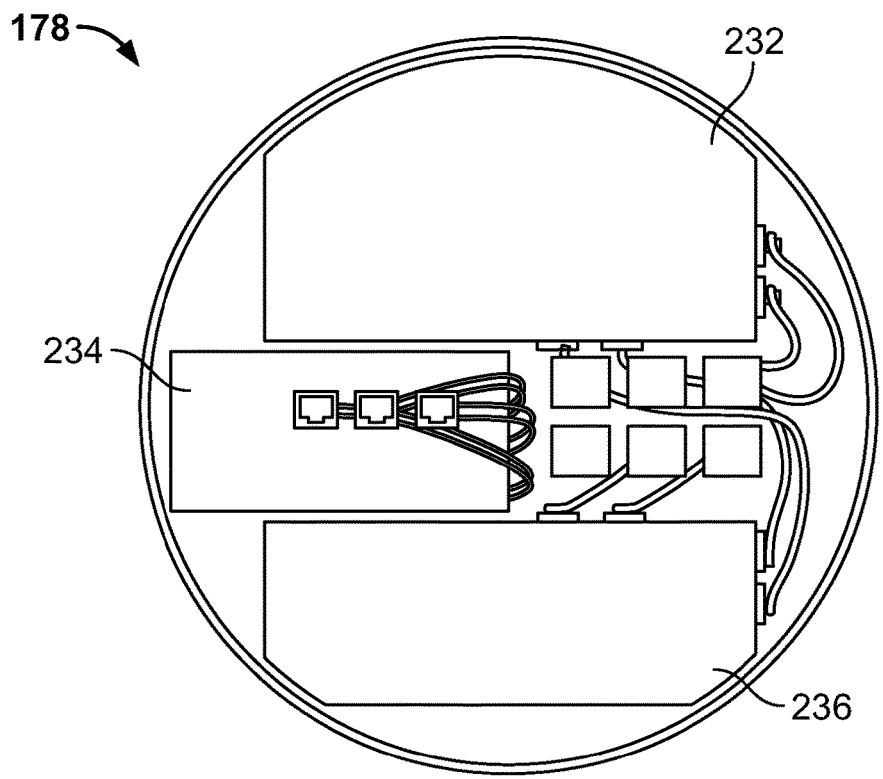
FIG. 19 is a top view of the device of FIG. 14 shown in greater detail.

FIG. 19 is a top view of the device 178 of FIG. 13 shown in greater detail. The device 178 includes a DC battery 232, a load controller 234, and a sandbox 236. The sandbox 236 is consistent with the sandbox explained in greater detail above and incorporated by reference above.

Figure 20:
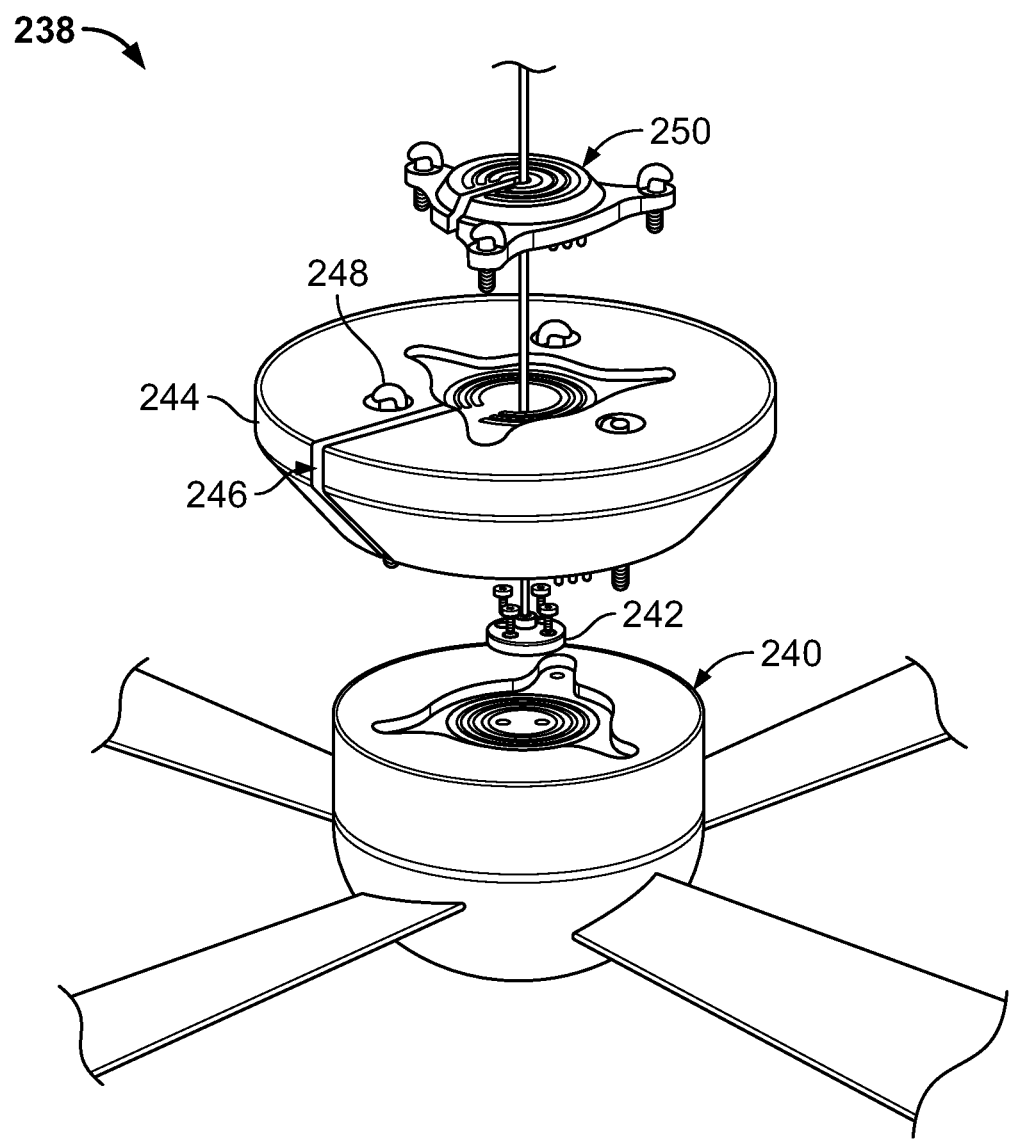
FIG. 20 is a perspective view of a ninth embodiment of an electrical fixture assembly of the present disclosure.

FIG. 20 is a perspective view of a ninth embodiment of an electrical fixture assembly 238 of the present disclosure. As can be seen, the assembly 238 can include a fan 240 as a final module mounted on the assembly 238. The assembly 238 can include a cable anchor 242 for mounting and securing the assembly 238 on the fan 240. The 240 is used for illustration purposes only and the final module can be any suitable device. The assembly 238 can include a device 244 which can be any device as described in the present disclosure. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices. The device 244 can include a slot 246 for mounting new modules or device after assembly. The device 244 can also include fold-away thumb screws 248 to secure other modules or devices on the device 244. The assembly 238 can include commutator-type electrical contacts which can be placed on the device 244.

Figure 21:
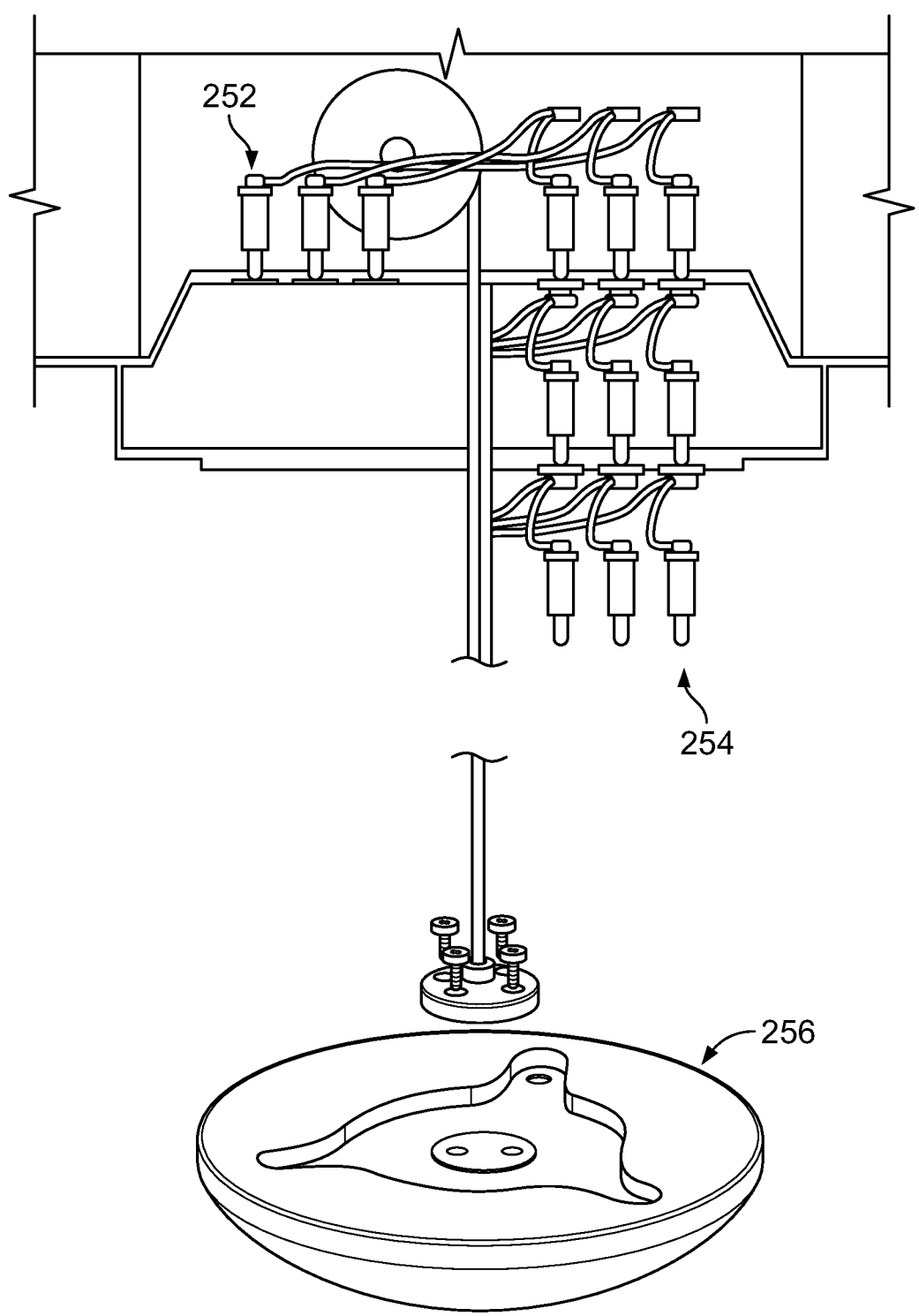
FIG. 21 is a cross-sectional view of the electrical fixture assembly of FIG. 20.

FIG. 21 is a cross-sectional view of the electrical fixture assembly of FIG. 20. The assembly 238 includes dual-spring pin contacts 252 for non-controlled orientation of the assembly 238. The assembly 238 can also include a single set of contacts 254 for oriented connection. Alternatively, a finishing end cap 256 can be provided for securing the assembly 238 when the fan 240 is not present.

Figure 22:
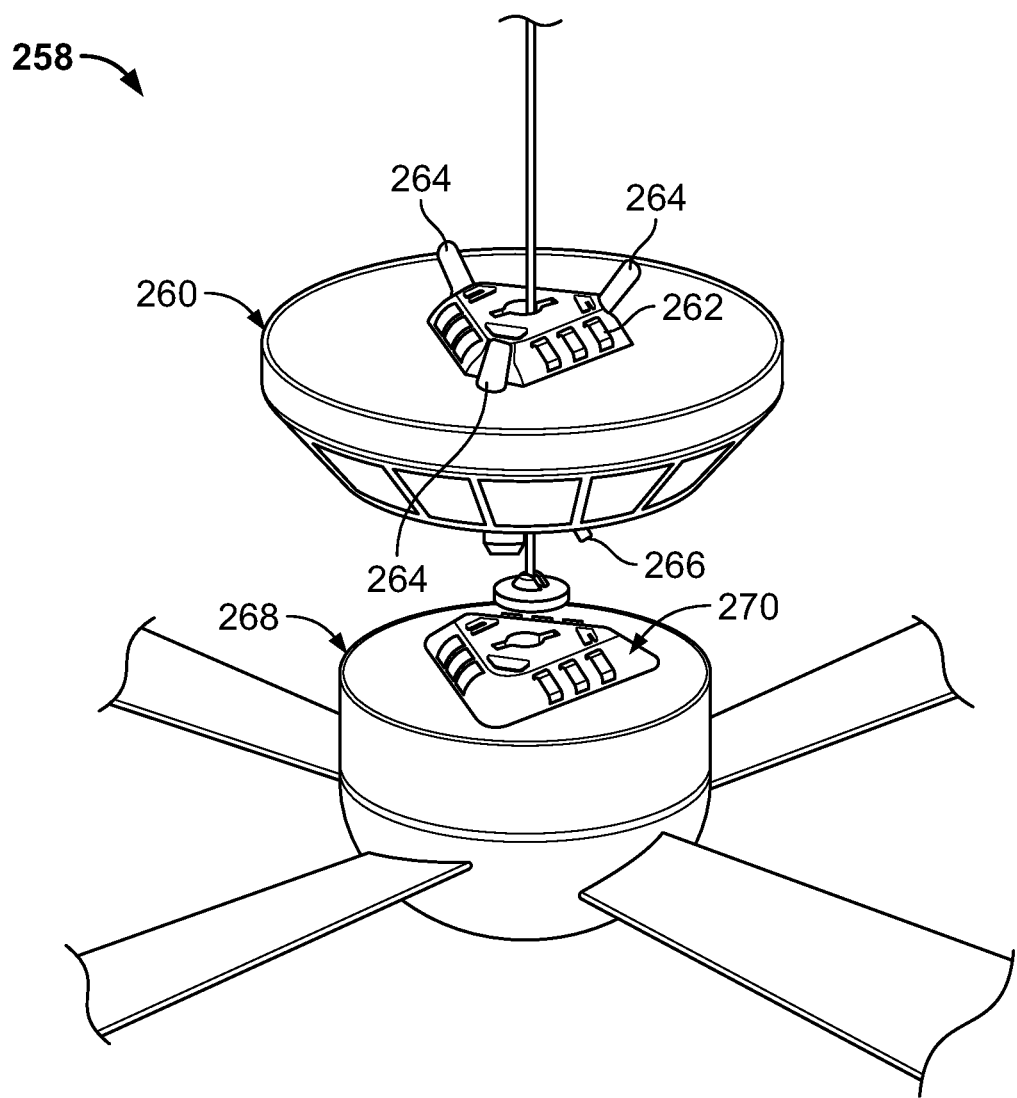
FIG. 22 is a perspective view of a tenth embodiment of an electrical fixture assembly of the present disclosure.

FIG. 22 is a is a perspective view of a tenth embodiment of an electrical fixture assembly 258 of the present disclosure. The assembly 258 can include a device 260, which can be any device described in the present disclosure. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices. The device 260 can include a plurality of spring contacts 262 and a plurality of clamps 264 for securing a module to the device 260. The device 260 can also include a hook 266 for securing a module/device underneath the device 260. The assembly 258 can further include a fan 268 having a self-orientating interface 270 for being secured to the assembly 258.

Figure 23:
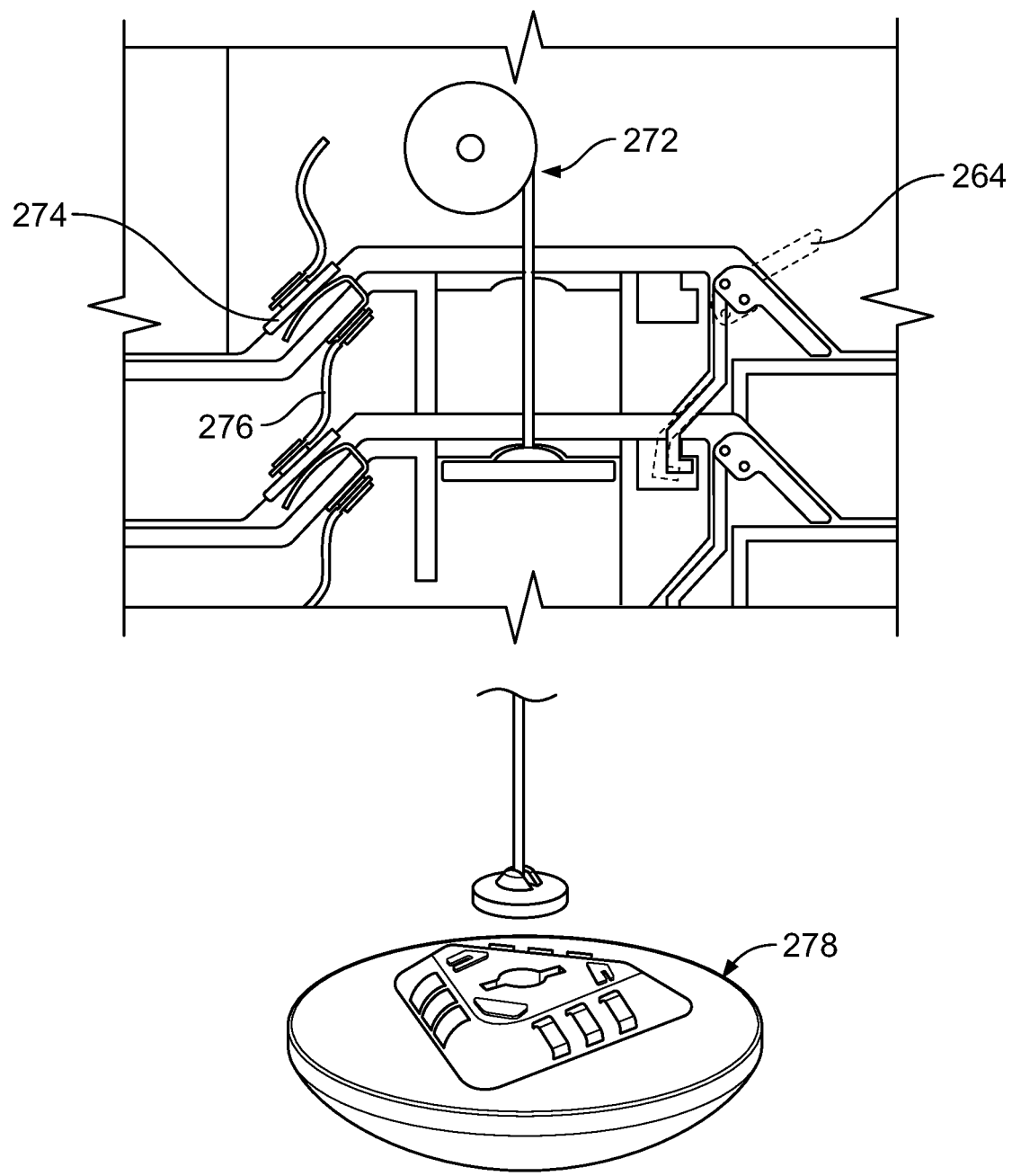
FIG. 23 is a cross-sectional view of the electrical fixture assembly of FIG. 22.

FIG. 23 is a cross-sectional view of the electrical fixture assembly 258 of FIG. 22. The assembly 258 includes a cable reel 272 for vertically adjusting a cable connecting a plurality of device in the assembly 258. The spring contacts 262 can include a contact plate and thru wiring 272 to allow for electrical communication between the device 260 and another device. The assembly 258 can further include a finishing end cap 278 if the fan 268 is not desired or present.

Figure 24:
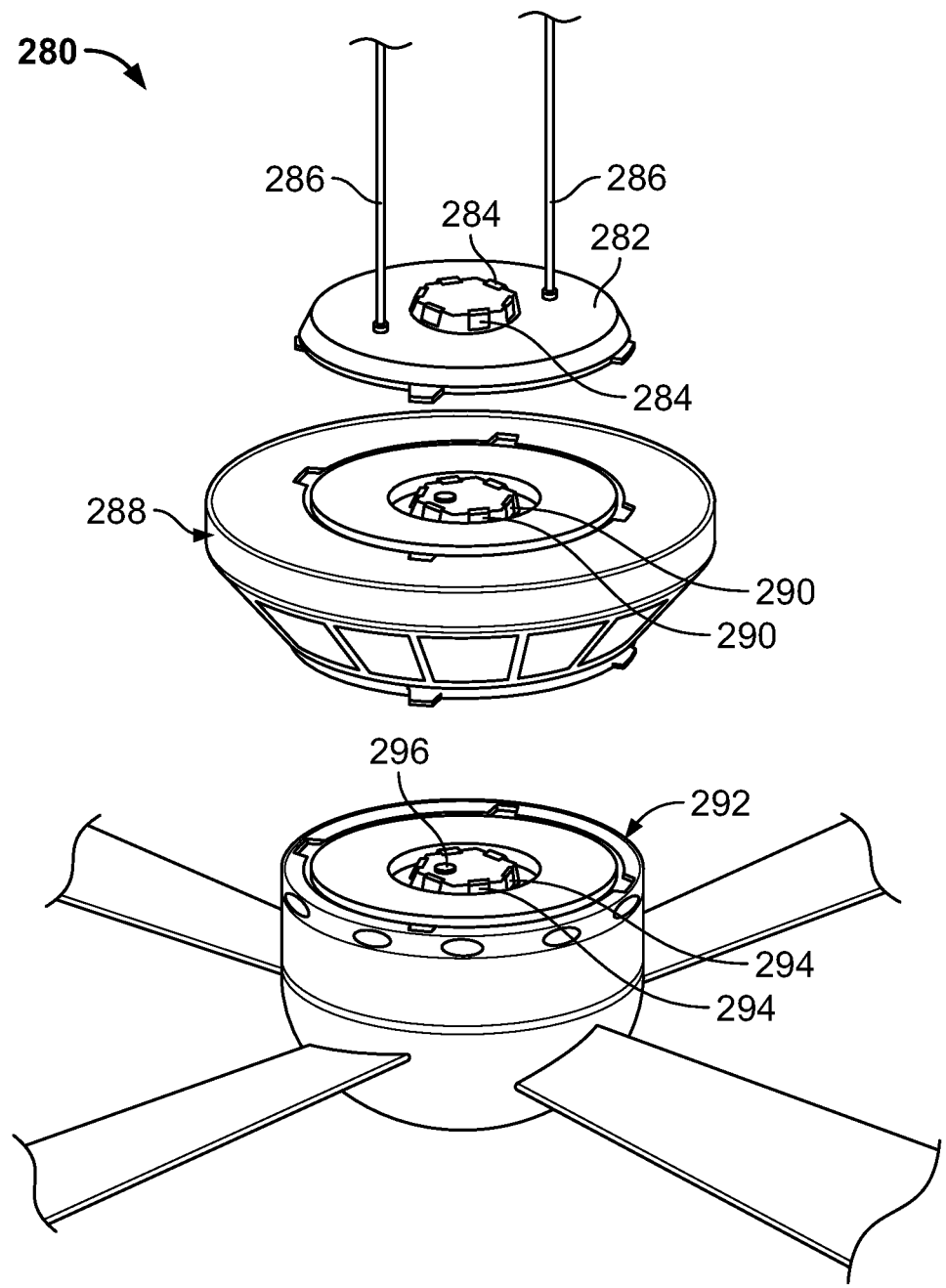
FIG. 24 is a perspective view of a eleventh embodiment of an electrical fixture assembly of the present disclosure.

FIG. 24 is a perspective view of a eleventh embodiment of an electrical fixture assembly 280 of the present disclosure. The assembly 280 includes a support cap 282 having a plurality of leaf-spring contacts 284 and dual-orientating cables 286. The assembly 280 further includes a collar 288 having a plurality of leaf-spring contacts 290. The assembly 280 can also include a fan 292 having a plurality of leaf contacts 294 and a module orientation feature 296. The collar 288 can be rotated to lock and unlock a plurality of devices that can be used in the assembly 280. These devices include, but are not limited to, a load control device, coordinator device, security device, safety device, enhanced vision device, motion detection, biometric device, thermal detection device, daylight harvesting device, CO2/carbon reduction device, energy efficiency device, renewable energy device, water utilization device, natural resource conservation device, identification of wastage device, health and wellness devices, ambient monitoring and control devices, air quality devices, lighting devices, reduction of cancer devices, detoxification/air-purification devices, vertical farming devices, low impact food-supply chain devices, control of vertical greenhouse gases devices, and skilled work force devices. In the example of FIG. 24, the collar 288 can rotate clockwise or counterclockwise to unlock and lock the fan 292 and the cap 282.

Figure 25:
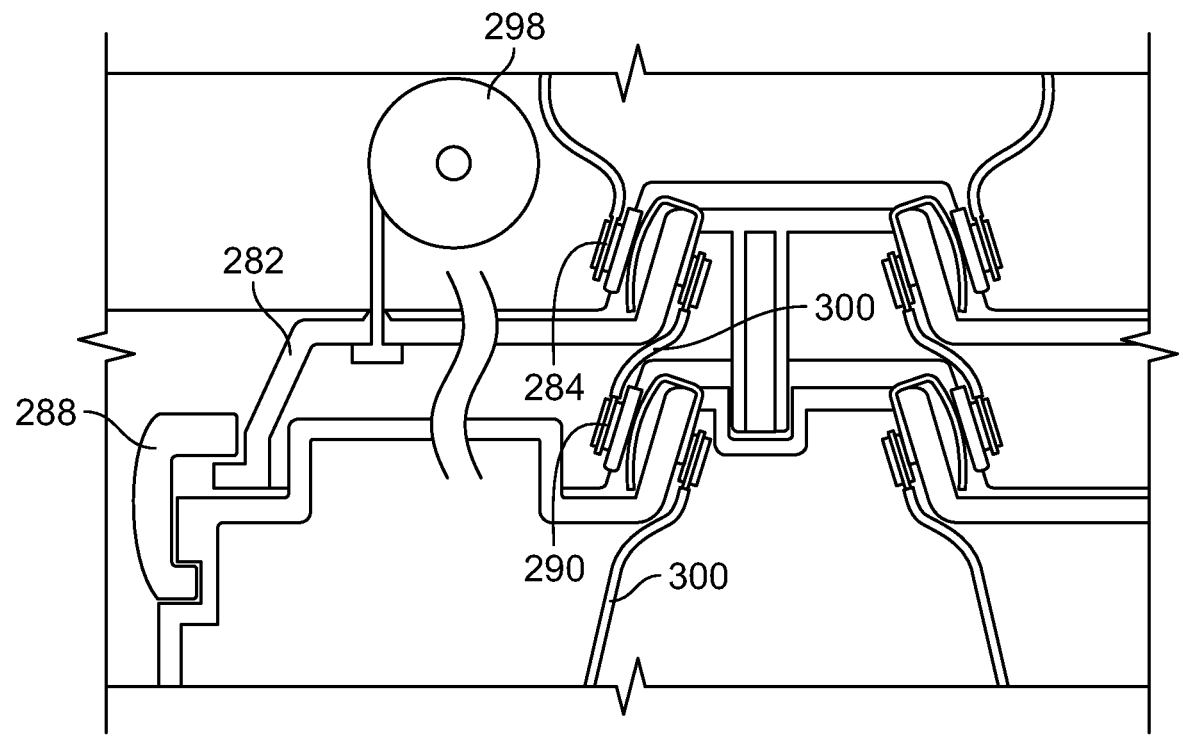
FIG. 25 is a cross-sectional view of the electrical fixture assembly of FIG. 24.
Figure 25:
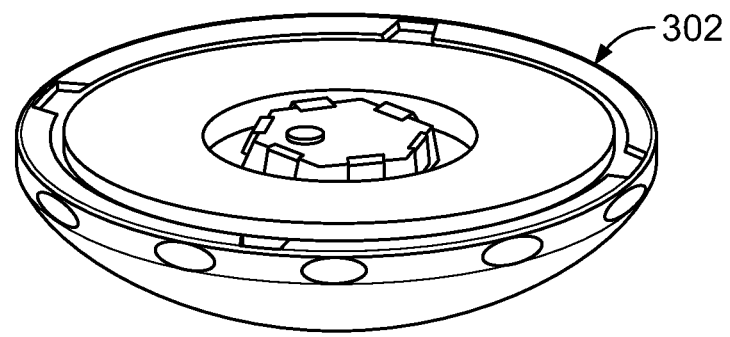

FIG. 25 is a cross-sectional view of the electrical fixture assembly of FIG. 24. The assembly 280 includes a cable reel 298 for controlling the cables 286. As can be seen, the plurality of leaf contacts 284 can be in electrical communication with the plurality of leaf contacts 290 through the internal wiring 300. The assembly 280 can further include a finishing end cap 302 if the fan 292 is not desired or present.

Figure 26:
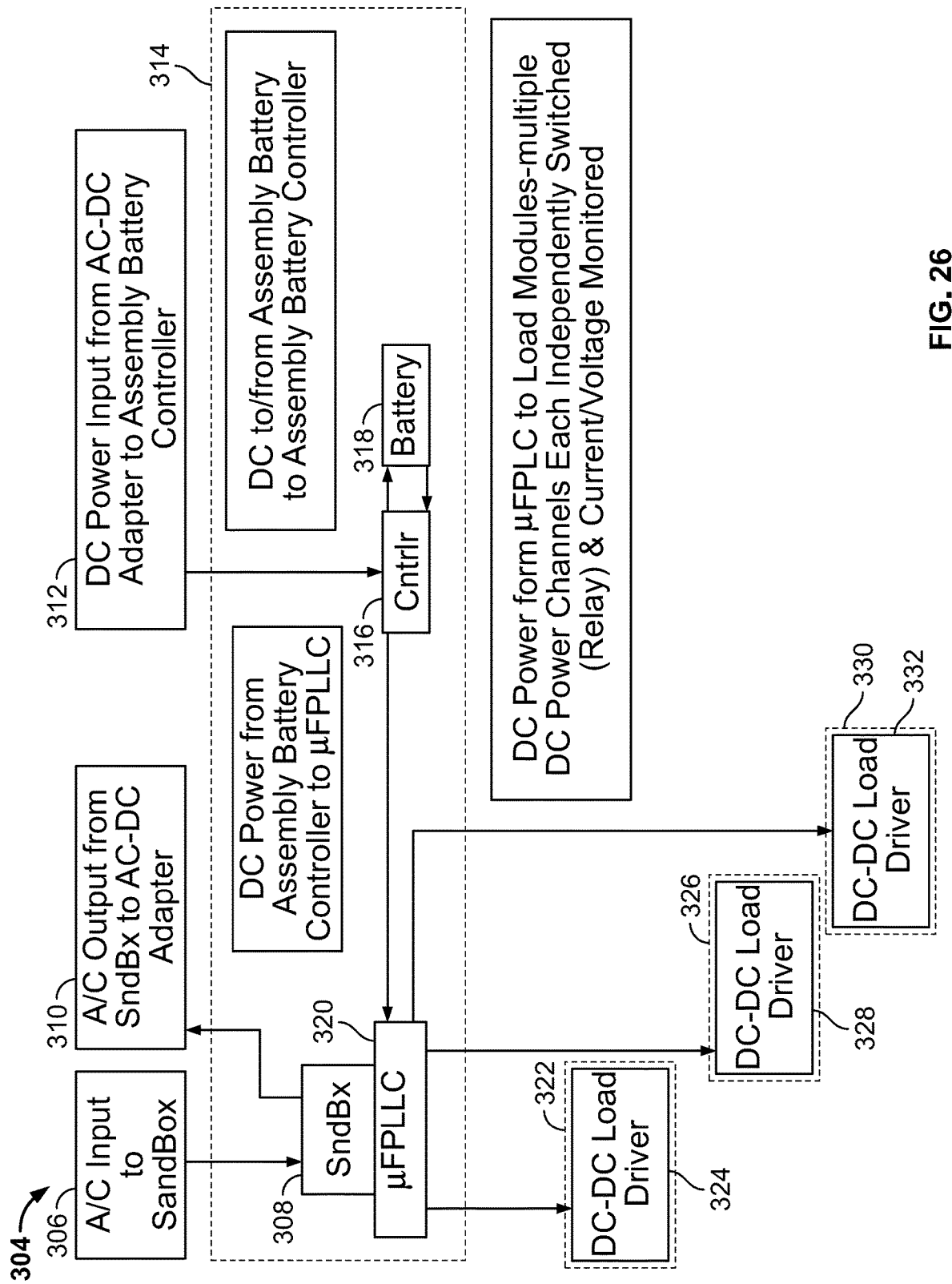
FIG. 26 is a block diagram showing the flow of electrical signals in the present disclosure.

FIG. 26 is a block diagram showing the flow of electrical signals in the present disclosure. The assemblies of the present disclosure can receive an AC input 306, which can flow to the sandbox 308. The sandbox can output an AC signal to an AC-DC adapter 310. The assemblies of the present disclosure can send DC power in module 312 from the AC-DC adapter 310 to a top module 314 and in particular, top a controller 316. The controller 316 can be in communication with a battery 318. The controller 316 can send DC power to the uFPLC 320. The uFPLC can send DC power to a first module 322 having a first DC-DC load driver 324, a second module 326 having a second DC-DC load driver 328, and a third module 330 having a first DC-DC load driver 332. This electrical arrangement can apply to all of the embodiments of the present disclosure.

Having thus described the system and method in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

The invention claimed is:

1. A multipurpose electrical assembly comprising:
an antenna extending vertically downward from a ceiling for receiving a plurality of devices;
a hydraulic lift being operable to move the antenna in a vertical direction;
wherein the antenna receives electrical power from a power source in the ceiling and distributes power to the plurality of devices;
wherein the plurality of devices can be arranged in any order.

2. The assembly of claim 1, wherein one of the plurality of devices is a HINS light for sanitizing air.

3. The assembly of claim 1, wherein one of the plurality of devices is a LED light.

4. The assembly of claim 1, wherein a lowest of the plurality of devices includes an attachment portion for receiving a drone on the assembly.

5. The assembly of claim 1, wherein one of the plurality of devices is a smoke detector.

6. The assembly of claim 1, wherein one of the plurality of devices is a LED glass light.

7. The assembly of claim 1, wherein one of the plurality of devices is a speaker.

8. The assembly of claim 1, wherein one of the plurality of devices is a LED torch light.

9. The assembly of claim 1, further comprising a process load controller for controlling the load among the plurality of devices.

10. A multipurpose electrical assembly comprising:
a plurality of devices each having a connector on a first surface for connecting to the assembly and a plurality of pins on a second opposing surface for receiving a device to be connected to the assembly;
a member mechanically fastened to a ceiling having a plurality of pins for receiving a first device of the plurality of devices;
wherein the connector of the plurality of devices receives electrical power from a preceding device and transfers electrical power to a following device through the plurality of pins; and
wherein the plurality of devices can be arranged in any order.

11. The assembly of claim 10, wherein one of the plurality of devices is a HINS light for sanitizing air.

12. The assembly of claim 10, wherein one of the plurality of devices is a LED light.

13. The assembly of claim 10, wherein a lowest of the plurality of devices includes an attachment portion for receiving a drone on the assembly.

14. The assembly of claim 10, wherein one of the plurality of devices is a smoke detector.

15. The assembly of claim 10, wherein one of the plurality of devices is a coordinator.

16. The assembly of claim 10, wherein one of the plurality of devices is a speaker.

17. The assembly of claim 10, wherein one of the plurality of devices is a fan.

18. The assembly of claim 10, further comprising a process load controller for controlling the load among the plurality of devices.

19. A lighting system comprising:
a plurality of recesses in a ceiling having a first connector;
a plurality of drones having a LED light and a second connector for connecting to the first connector and docking in the recess; and
a remote computer system for automatically controlling the plurality of drones to dock in the recess where light is required.

20. The lighting system of claim 19 further comprising a remote control for manually controlling the plurality of drones.

21. The lighting system of claim 19 further comprising a mobile device for manually controlling the plurality of drones.

22. The lighting system of claim 19, wherein the mobile device can view a live feed of a camera on each of the plurality of drones.

23. The lighting system of claim 19, wherein the drone in configured to rotate in a circular fashion and thread into a threaded mating connection in the recess.

24. The lighting system of claim 19, wherein the drone is configured to mechanically connect to the recess via a mechanical snap-fit connection.

25. The lighting system of claim 19, wherein the drone is configured to release itself from a first recess of the plurality of recesses and move to a second recess where light is required.

26. The lighting system of claim 19, wherein the drone is configured to change its shape to connect to recesses with different arrangements.

27. A multipurpose electrical assembly comprising: a cable extending vertically downward from a ceiling;
a power lift being operable to move the cable in a vertical direction;
a plurality of devices mechanically fastened with a plurality of superstack devices; and wherein the plurality of devices can be arranged in any order.

28. The assembly of claim 27, wherein one of the plurality of devices is a HINS light for sanitizing air.

29. The assembly of claim 27, wherein one of the plurality of devices is a LED light.

30. The assembly of claim 27, wherein a lowest of the plurality of devices includes an attachment portion for receiving a drone on the assembly.

31. The assembly of claim 27, wherein one of the plurality of devices is a smoke detector.

32. The assembly of claim 27, wherein one of the plurality of devices is a coordinator.

33. The assembly of claim 27, wherein one of the plurality of devices is a speaker.

34. The assembly of claim 27, wherein one of the plurality of devices is a fan.

35. The assembly of claim 27, wherein the cable is mounted to a superconduit on the ceiling.

36. The assembly of claim 27, further comprising a process load controller for controlling the load among the plurality of devices.

37. A multipurpose electrical assembly comprising:
a module receiving an alternating current from a power source in a ceiling and converting the alternating current source to a direct current source;
a plurality of devices each having a first connector on a first surface for connecting to the assembly and receiving electrical power from a preceding device and a second connector on a second opposing surface for receiving a following device to be connected to the assembly and for transferring electrical power to the following device;
wherein a first device of the plurality of devices attaches to the
module; and wherein the plurality of devices can be arranged in
any order.

38. The assembly of claim 37, wherein one of the plurality of devices is a HINS light for sanitizing air.

39. The assembly of claim 37, wherein one of the plurality of devices is a LED light.

40. The assembly of claim 37, wherein a lowest of the plurality of devices includes an attachment portion for receiving a drone on the assembly.

41. The assembly of claim 37, wherein one of the plurality of devices is a smoke detector.

42. The assembly of claim 37, wherein one of the plurality of devices is a coordinator.

43. The assembly of claim 37, wherein one of the plurality of devices is a speaker.

44. The assembly of claim 37, wherein one of the plurality of devices is a fan.

45. The assembly of claim 37, wherein the first connector and the second connector comprise of spring contacts.

46. The assembly of claim 37, wherein the first connector and the second connector comprise of contact plates.

47. The assembly of claim 37, further comprising a process load controller for controlling the load among the plurality of devices.

* * * * *